(12) United States Patent
Gerber

(10) Patent No.: US 7,765,012 B2
(45) Date of Patent: Jul. 27, 2010

(54) IMPLANTABLE MEDICAL DEVICE INCLUDING A CONDUCTIVE FIXATION ELEMENT

(75) Inventor: Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 301 days.

(21) Appl. No.: 11/606,626

(22) Filed: Nov. 30, 2006

(65) Prior Publication Data

US 2008/0132981 A1    Jun. 5, 2008

(51) Int. Cl.
*A61N 1/00* (2006.01)
(52) U.S. Cl. ..................................................... 607/116
(58) Field of Classification Search .......... 607/116–118
See application file for complete search history.

(56) References Cited

U.S. PATENT DOCUMENTS

| | | | |
|---|---|---|---|
| 4,103,690 A | | 8/1978 | Harris |
| 4,112,952 A | | 9/1978 | Thomas et al. |
| 5,249,574 A | | 10/1993 | Bush et al. |
| 5,255,678 A | | 10/1993 | Deslauriers et al. |
| 5,255,679 A | | 10/1993 | Imran |
| 5,265,608 A | | 11/1993 | Lee et al. |
| 5,282,845 A | * | 2/1994 | Bush et al. ................... 607/128 |
| 5,314,462 A | | 5/1994 | Heil, Jr. et al. |
| 5,358,514 A | * | 10/1994 | Schulman et al. .............. 607/61 |
| 5,492,119 A | | 2/1996 | Abrams |
| 5,540,734 A | | 7/1996 | Zabara |
| 5,545,219 A | | 8/1996 | Kuzma |
| 5,766,234 A | | 6/1998 | Chen et al. |
| 5,840,076 A | | 11/1998 | Swanson et al. |
| 5,860,974 A | | 1/1999 | Abele |
| 6,074,401 A | | 6/2000 | Gardiner et al. |
| 6,149,658 A | | 11/2000 | Gardiner et al. |
| 6,266,568 B1 | | 7/2001 | Mann et al. |
| 6,308,105 B1 | | 10/2001 | Duysens et al. |
| 6,352,561 B1 | * | 3/2002 | Leopold et al. ............ 623/1.23 |
| 6,477,423 B1 | | 11/2002 | Jenkins |
| 6,505,075 B1 | | 1/2003 | Weiner |
| 6,510,332 B1 | | 1/2003 | Greenstein |
| 6,514,265 B2 | | 2/2003 | Ho et al. |
| 6,529,777 B1 | | 3/2003 | Holmström et al. |
| 6,551,332 B1 | | 4/2003 | Nguyen et al. |
| 6,589,238 B2 | | 7/2003 | Edwards et al. |
| 6,600,955 B1 | | 7/2003 | Zierhofer |
| 6,607,541 B1 | | 8/2003 | Gardiner et al. |

(Continued)

OTHER PUBLICATIONS

Notification of Transmittal of the International Search Report and the Written Opinion for corresponding patent application No. PCT/US2007/001938, mailed Aug. 7, 2007, 12 pages.

(Continued)

*Primary Examiner*—George Manuel
(74) *Attorney, Agent, or Firm*—Scott A. Marks

(57) ABSTRACT

A system comprises an implantable medical device and an actively deployable clip attached to the implantable medical device to restrict movement of the implantable medical device once the clip is deployed within a body of a patient. The clip includes an electrically conductive portion. The implantable medical device may be implanted proximate to any suitable tissue site within the patient, and in one embodiment, the implantable medical device is implanted proximate to an occipital nerve or a trigeminal nerve of the patient.

35 Claims, 10 Drawing Sheets

U.S. PATENT DOCUMENTS

| | | | |
|---|---|---|---|
| 6,613,059 B2 | 9/2003 | Schaller et al. | |
| 6,641,593 B1 | 11/2003 | Schaller et al. | |
| 6,695,859 B1 | 2/2004 | Golden et al. | |
| 6,876,885 B2 | 4/2005 | Swoyer et al. | |
| 6,889,093 B1 | 5/2005 | Flammang | |
| 6,895,283 B2 | 5/2005 | Erickson et al. | |
| 6,913,607 B2 | 7/2005 | Ainsworth et al. | |
| 6,918,917 B1 | 7/2005 | Nguyen et al. | |
| 6,921,407 B2 | 7/2005 | Nguyen et al. | |
| 6,926,730 B1 | 8/2005 | Nguyen et al. | |
| 6,960,221 B2 | 11/2005 | Ho et al. | |
| 7,047,084 B2 | 5/2006 | Erickson et al. | |
| 7,054,692 B1 | 5/2006 | Whitehurst et al. | |
| 7,099,718 B1 | 8/2006 | Thacker et al. | |
| 7,177,702 B2 | 2/2007 | Wallace et al. | |
| 7,181,288 B1 | 2/2007 | Rezai et al. | |
| 7,288,096 B2 | 10/2007 | Chin | |
| 2002/0103521 A1 | 8/2002 | Swoyer et al. | |
| 2002/0111659 A1 | 8/2002 | Davis et al. | |
| 2002/0156513 A1 | 10/2002 | Borkan | |
| 2003/0036790 A1 | 2/2003 | Corbett, III et al. | |
| 2003/0069623 A1 | 4/2003 | Stypulkowski | |
| 2003/0078603 A1 | 4/2003 | Schaller et al. | |
| 2003/0093118 A1 | 5/2003 | Ho et al. | |
| 2003/0093130 A1 | 5/2003 | Stypulkowski | |
| 2003/0120328 A1 | 6/2003 | Jenkins et al. | |
| 2003/0199974 A1 | 10/2003 | Lee et al. | |
| 2004/0059393 A1 | 3/2004 | Policker et al. | |
| 2004/0093053 A1 | 5/2004 | Gerber et al. | |
| 2004/0102797 A1 | 5/2004 | Golden et al. | |
| 2004/0111099 A1 | 6/2004 | Nguyen et al. | |
| 2004/0111139 A1 | 6/2004 | McCreery | |
| 2004/0116992 A1 | 6/2004 | Wardle et al. | |
| 2004/0193229 A1 | 9/2004 | Starkebaum et al. | |
| 2004/0230279 A1* | 11/2004 | Cates et al. | 607/126 |
| 2004/0243206 A1* | 12/2004 | Tadlock | 607/116 |
| 2005/0021054 A1 | 1/2005 | Ainsworth et al. | |
| 2005/0060014 A1 | 3/2005 | Swoyer et al. | |
| 2005/0065601 A1 | 3/2005 | Lee et al. | |
| 2005/0070924 A1 | 3/2005 | Schaller et al. | |
| 2005/0102006 A1* | 5/2005 | Whitehurst et al. | 607/46 |
| 2005/0107861 A1 | 5/2005 | Harris et al. | |
| 2005/0149141 A1 | 7/2005 | Starkebaum | |
| 2005/0149142 A1 | 7/2005 | Starkebaum | |
| 2005/0209653 A1 | 9/2005 | Herbert et al. | |
| 2005/0222632 A1 | 10/2005 | Obino | |
| 2005/0245986 A1 | 11/2005 | Starkebaum | |
| 2005/0246004 A1 | 11/2005 | Cameron et al. | |
| 2006/0079943 A1* | 4/2006 | Narciso, Jr. | 607/39 |
| 2006/0079950 A1 | 4/2006 | Lehnhardt et al. | |
| 2006/0206166 A1 | 9/2006 | Weiner | |
| 2006/0241733 A1 | 10/2006 | Zhang et al. | |
| 2006/0271137 A1 | 11/2006 | Stanton-Hicks | |
| 2007/0027514 A1 | 2/2007 | Gerber | |
| 2007/0027515 A1 | 2/2007 | Gerber | |

OTHER PUBLICATIONS

United States Patent Application entitled "Sutureless Implantable Medical Device Fixation," U.S. Appl. No. 11/413,071, filed Apr. 27, 2006.

Office Action for U.S. Appl. No. 11/606,774, mailed Dec. 24, 2008, 16 pages.

Response to Office Action for U.S. Appl. No. 11/413,071, filed Sep. 2, 2009, 13 pages.

Office Action for U.S. Appl. No. 11/606,774, dated Jul. 10, 2009, 11 pages.

Response to Office Action for U.S. Appl. No. 11/606,774, filed Sep. 10, 2009, 8 pages.

Office Action for U.S. Appl. No. 11/413,071, mailed Jun. 2, 2009, 10 pages.

Office Action from U.S. Appl. No. 11/606,774, dated Jan. 7, 2010, 14 pp.

Response to Office Action dated Jan. 7, 2010, from U.S. Appl. No. 11/606,774, filed Apr. 7, 2010, 17 pp.

Final Office Action for U.S. Appl. No. 11/413,071, mailed Jan. 12, 2010, 11 pages.

Response to Final Office Action for U.S. Appl. No. 11/413,071, filed Apr. 12, 2010, 12 pages.

Notification Concerning Transmittal of Copy of International Preliminary Report on Patentability for corresponding patent application No. PCT/US2007/001938, mailed Jun. 11, 2009, 8 pages.

* cited by examiner

IMPLANTABLE MEDICAL DEVICE INCLUDING A CONDUCTIVE FIXATION ELEMENT

TECHNICAL FIELD

The invention relates to implantable medical devices and, more particularly, to techniques for fixation of implantable medical devices within a body of a patient.

BACKGROUND

Electrical stimulation systems may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, muscle stimulation (e.g., functional electrical stimulation (FES) of muscles) or obesity. An electrical stimulation system typically includes one or more stimulation leads coupled to an electrical stimulator.

The neurostimulation lead may be percutaneously or surgically implanted in a patient on a temporary or permanent basis such that at least one stimulation electrode is positioned proximate to a target stimulation site. The target stimulation site may be, for example, a nerve or other tissue site, such as an occipital nerve, spinal cord, pelvic nerve, pudendal nerve, stomach, bladder, or within a brain or other organ of a patient, or within a muscle or muscle group of a patient.

Electrical stimulation of a peripheral nerve, such as stimulation of an occipital nerve or a trigeminal nerve, may be used to induce paresthesia. Occipital nerves, such as a lesser occipital nerve, greater occipital nerve or third occipital nerve, exit the spinal cord at the cervical region, extend upward and toward the sides of the head, and pass through muscle and fascia to the scalp. Pain caused by an occipital nerve, e.g. occipital neuralgia, may be mitigated by delivering stimulation therapy to the occipital region via an implanted stimulation lead.

In many electrical stimulation applications, it is desirable for a stimulation lead to resist migration following implantation. For example, it may be desirable for the electrodes disposed at a distal end of the implantable medical lead to remain proximate to a target stimulation site in order to provide adequate and reliable stimulation of the target stimulation site. In some applications, it may also be desirable for the electrodes to remain substantially fixed in order to maintain a minimum distance between the electrode and a nerve in order to help prevent inflammation to the nerve and in some cases, unintended nerve damage. Securing the stimulation lead at the target stimulation site may minimize lead migration.

SUMMARY

In general, the invention is directed to techniques for fixation of an implantable medical device, such as an electrical stimulator, lead or catheter, via an actively deployable fixation clip that is coupled to the implantable medical device. The fixation clip is configured to change from a first shape in an undeployed state to a second shape in a deployed state. In the deployed state, the fixation clip is configured to engage with surrounding tissue to substantially fix a position of the implantable medical device proximate to a target tissue site within a patient. In one embodiment, the target tissue site is an occipital nerve, a trigeminal nerve, and/or branches of the occipital and trigeminal nerves of a patient.

In accordance with one aspect of the invention, the fixation clip is attached directly or indirectly to a lead that is configured to deliver electrical stimulation therapy from an electrical stimulation generator to a target stimulation site within a patient. In one embodiment, the fixation clip includes an electrically conductive portion, such as a portion comprising a shape memory metal, which may be an electrode of the lead. The electrically conductive fixation clip may substantially fix a position of the lead as well as deliver electrical stimulation to the target stimulation site within a patient.

In one embodiment, the invention is directed to system comprising an implantable medical device and a fixation element coupled to the implantable medical device. The fixation element comprises an electrically conductive portion configured to at least one of deliver electrical stimulation to a target tissue site within a patient or sense a physiological parameter from the target tissue site. The fixation element is actively deployable from a first shape to a second shape to resist substantial movement of the implantable medical device from the target tissue site.

In another embodiment, the invention is directed to a medical lead comprising a lead body, an electrical conductor disposed within the lead body, and a fixation element comprising an electrically conductive portion electrically coupled to the electrical conductor. The fixation element is actively deployable from a first shape to a second shape to resist substantial movement of the lead body from a target therapy delivery site in a patient.

In yet another embodiment, the invention is directed to a method comprising implanting an implantable medical device in a body of a patient, and actively deploying a fixation element coupled to the implantable medical device. The fixation element comprises an electrically conductive portion configured to at least one of deliver electrical stimulation to a target tissue site within the body of the patient or sense a physiological parameter from the target tissue site. The fixation element is actively deployable from a first shape to a second shape to resist substantial movement of the implantable medical device from the target tissue site.

The details of one or more embodiments of the invention are set forth in the accompanying drawings and the description below. Other features, objects, and advantages of the invention will be apparent from the description and drawings, and from the claims.

DETAILED DESCRIPTION

The present invention relates to actively deployable clips for fixing an implantable medical device proximate to a target tissue site within a patient. The implantable medical device is configured to deliver a therapy to the target tissue site. Various embodiments of the implantable medical device may be applicable to different therapeutic applications. In some embodiments, the implantable medical device is configured to couple to a therapy delivery source, such as an electrical stimulation generator or a fluid delivery device. For example, the implantable medical device may be a stimulation lead or a lead extension that is used to deliver electrical stimulation to a target stimulation site and/or sense parameters (e.g., blood pressure, temperature or electrical activity) proximate to a target site within a patient. In another embodiment, the implantable medical device may be a catheter that is placed to deliver a fluid, such as pharmaceutical agents, insulin, pain relieving agents, gene therapy agents or the like from a fluid delivery device (e.g., a fluid reservoir and/or pump) to the target tissue site within the patient. In yet another embodiment, the implantable medical device may be a microstimulator that may be implanted within tissue of a patient to deliver stimulation to the tissue. Thus, in some embodiments, "therapy" may include stimulation therapy, sensing or monitoring of one or more physiological parameters, fluid delivery, and the like. "Target tissue site" refers generally to the target site for implantation of an elongated member, regardless of the type of therapy.

The invention is applicable to any configuration or type of implantable medical device that is used to deliver therapy to a nerve, organ, muscle, muscle group, or other tissue within a patient. For purposes of illustration, however, the disclosure will refer to a neurostimulation lead.

In one embodiment, the target tissue site is proximate to an occipital nerve site or trigeminal nerve site within a patient, such as tissue adjacent to the occipital nerve or the trigeminal nerve or a nerve branching from the occipital and/or trigeminal nerve. Thus, reference to an "occipital nerve" or a "trigeminal nerve" throughout the disclosure also includes branches of the occipital and trigeminal nerves, respectively. In addition, the therapy may be delivered to both an occipital nerve and trigeminal nerve within the patient.

Figure 1:
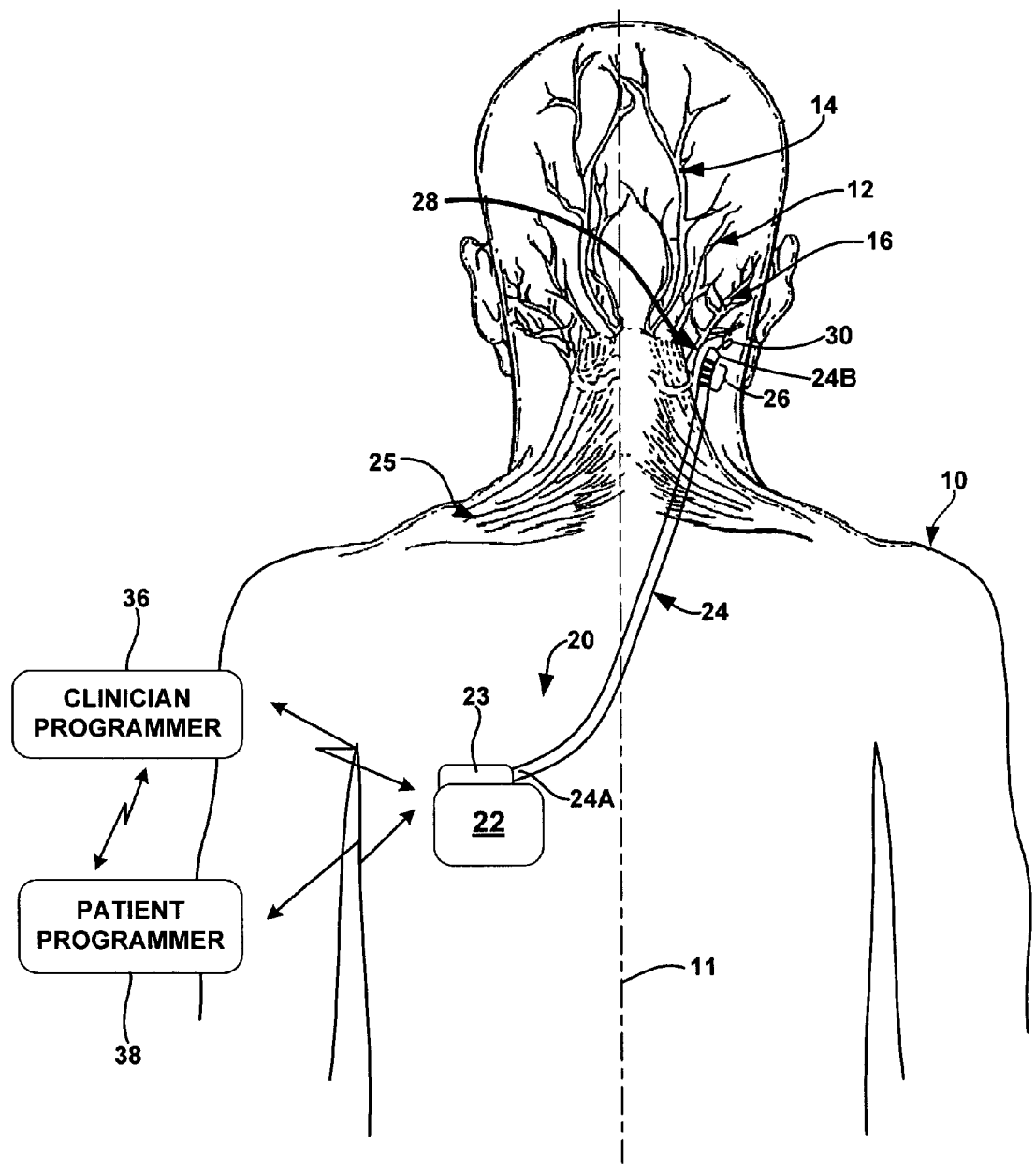
FIG. 1 is a schematic view of a therapy system including a lead fixed proximate to an occipital nerve of a patient via an actively deployable fixation clip.

FIG. 1 is a schematic view of a head and torso of patient 10, in which of a lesser occipital nerve 12, greater occipital nerve 14, and third occipital nerve 16 of patient 10 are shown. Occipital nerves 12, 14, and 16 generally extend upward from a spinal cord of patient 10 to the back and sides of the head. Also shown in FIG. 1 is therapy system 20, which includes electrical stimulator 22 and implantable medical lead 24, which extends between proximal end 24A and distal end 24B, and includes stimulation electrodes 26 proximate to distal end 24B. Electrical stimulator 22 provides electrical stimulation via one or more electrodes 26 of lead 24 to target stimulation site 28, which in the embodiment shown in FIG. 1, may be adjacent to at least one of lesser occipital nerve 12, greater occipital nerve 14 or third occipital nerve 16 of patient 10. In the embodiment shown in FIG. 1, electrodes 26 of lead 24 are implanted proximate to third occipital nerve 16. In alternate embodiments, lead 24 may be positioned proximate to one or more other peripheral nerves proximate to occipital nerves 12, 14, 16 of patient 10, such as nerves branching from occipital nerves 12, 14 or 16.

Stimulation of target stimulation site 28 (i.e., in regions of patient 10 proximate to occipital nerves 12, 14, and/or 16) may help alleviate pain associated with, for example, chronic migraines, cervicogenic headaches, occipital neuralgia or trigeminal neuralgia.

In the embodiment shown in FIG. 1, electrical stimulator 22 is a neurostimulator that is either implantable or external. FIG. 1 illustrates neurostimulator 22 implanted within a chest cavity of patient 10. In other embodiments, neurostimulator 22 may be implanted in any suitable location of patient 10. For example, neurostimulator 22 may be subcutaneously implanted in the body of patient 10 within a lower back, lower abdomen, proximate to the trapezius muscle 25 of patient 10, or buttocks of patient 10. Neurostimulator 22 provides a programmable stimulation signal (e.g., in the form of electrical pulses or substantially continuous-time signals) that is delivered to target stimulation site 28 by implantable medical lead 24, and more particularly, via one or more stimulation electrodes 26 carried by lead 24. Neurostimulator 22 may also be referred to as a pulse generator. In some embodiments, lead 24 may also carry one or more sense electrodes to permit neurostimulator 22 to sense electrical signals from target stimulation site 28.

In some embodiments, neurostimulator 22 may be coupled to two or more leads, e.g., for bilateral or multi-lateral stimulation. For example, therapy system 20 may include two leads, where one lead is positioned proximate to a branch of occipital nerve 12, 14, or 16 on each side of the head of patient 10 (i.e., on each side of the midline) to achieve bilateral stimulation. Midline 11 is a schematic representation of the line that divides patient 10 into approximately equal and symmetrical left and right halves. Delivering therapy to two target tissue sites may be used to deliver therapy to two nerve branches that branch from the same nerve. Nerves may branch into left and right branches that extend to opposite sides of midline 11, and therapy is delivered to two nerve branches on opposite sides of midline 11. Stimulation of two nerve branches on opposite sides of midline 11 may be referred to as bilateral stimulation. However, bilateral stimulation may also refer to stimulation of any two regions of patient 10 either sequentially or simultaneously. Delivering therapy after nerves branch, e.g., closer to the nerve endings, may allow more targeted therapy delivery with fewer side effects.

Bilateral stimulation may also be achieved with a single lead 24, where electrodes 26 of lead 24 are positioned to span both regions of stimulation. For example, bilateral stimulation of an occipital nerve may be achieved by utilizing a single lead 24 that is placed such that electrodes 26 span both sides of the midline 11 of patient 10 and proximate to the branches of the occipital nerve to be stimulated.

Proximal end 24A of lead 24 may be both electrically and mechanically coupled to connector 23 of neurostimulator 22 either directly or indirectly (e.g., via a lead extension). In particular, conductors disposed within a lead body of lead 24 electrically connect stimulation electrodes 26 (and sense electrodes, if present) located adjacent to distal end 24B of lead 24 to neurostimulator 22. Proximal end 24A of lead 24 may include electrical contacts that correspond to each of the conductors that are electrically connected to electrodes 26, where the electrical contacts electrically couple electrodes 26 to neurostimulator 22.

Lead 24 further includes an actively deployable clip fixation element 30 attached to lead 24 to help substantially fix lead 24 proximate to target stimulation site 28. In FIG. 1, clip 30 is in a deployed state. Although one clip 30 is shown in FIG. 1 attached to distal end 24B of lead 24 and near electrodes 26, in other embodiments, lead 24 may include more than one or more clips arranged in any suitable fashion with respect to lead 24. Clip 30 may be formed from elastic, shape memory materials, or any other material that is capable of changing shape upon release of a retainer mechanism. In some embodiments, at least a portion of clip 30 may be electrically conductive, thereby enabling clip 30 to act as an electrode of lead 24. For example, clip 30 may be a sensing electrode or a stimulation electrode of lead 24.

As described in further detail below, actively deployable clip 30 may be deployed by releasing clip 30 from a retainer mechanism. For example, a retainer wrap, band or binder may be cut, broken or withdrawn to release clip 30. Deployment of actively deployable clip 30 by releasing it from retainer mechanism permits clip 30 to initiate a shape change due to general elasticity or shape memory properties. For example, clip 30 may change from a substantially straight or slightly curved shape, prior to deployment, to a moderately or highly curvilinear or spiral shape, following deployment, as shown in FIG. 1. The post-deployment shape of clip 30 may be a regular or irregular shape, provided that clip 30 assumes a shape that interacts and engages with body tissue to resist movement of lead 24. In particular, it is desirable for electrodes 26 to remain within an operative distance with respect to target stimulation site 28 following implantation of lead 24 within patient 10.

In other embodiments, target tissue site 28 (which may be a target therapy delivery site) may be a location proximate any suitable nerve, organ, muscle or muscle group within a patient, which may be selected based on, for example, a therapy program selected for a particular patient. For example, therapy system 20 may be used to deliver electrical stimulation therapy to a sacral nerve, a pudendal nerve, a perineal nerve, a trigeminal nerve or other areas of the nervous system, in which cases, lead 24 would be implanted and substantially fixed proximate to the respective nerve. As further examples, lead 24 may be positioned for temporary or chronic spinal cord stimulation for the treatment of pain, for peripheral neuropathy or post-operative pain mitigation, ilioinguinal nerve stimulation, intercostal nerve stimulation, gastric stimulation for the treatment of gastric mobility disorders and obesity, muscle stimulation (e.g., functional electrical stimulation (FES) of muscles), for mitigation of other peripheral and localized pain (e.g., leg pain or back pain), or for deep brain stimulation to treat movement disorders and other neurological disorders. Accordingly, although patient 10 and target stimulation site 28 of FIG. 1 are referenced throughout the remainder of the disclosure for purposes of illustration, a neurostimulation lead 24 in accordance with the invention may be adapted for use in a variety of electrical stimulation applications in addition to occipital nerve stimulation.

Therapy system 20 may also include clinician programmer 36 and patient programmer 38. Clinician programmer 36 may be a handheld computing device that permits a clinician to program electrical stimulation therapy for patient 10, e.g., using input keys and a display. For example, using clinician programmer 36, the clinician may specify electrical stimulation parameters for use in delivery of neurostimulation therapy. Clinician programmer 36 supports telemetry (e.g., radio frequency (RF) telemetry) with neurostimulator 22 to download neurostimulation parameters and, optionally, upload operational or physiological data stored by neurostimulator 22. In this manner, the clinician may periodically interrogate neurostimulator 22 to evaluate efficacy and, if necessary, modify the stimulation parameters.

Like clinician programmer 36, patient programmer 38 may be a handheld computing device. Patient programmer 38 may also include a display and input keys to allow patient 10 to interact with patient programmer 38 and neurostimulator 22. In this manner, patient programmer 38 provides patient 10 with an interface for control of neurostimulation therapy by neurostimulator 22. For example, patient 10 may use patient programmer 38 to start, stop or adjust neurostimulation therapy. In particular, patient programmer 38 may permit patient 10 to adjust stimulation parameters such as duration, amplitude, pulse width and pulse rate, within an adjustment range specified by the clinician via clinician programmer 38, or select from a library of stored stimulation therapy programs.

Neurostimulator 22, clinician programmer 36, and patient programmer 38 may communicate via cables or a wireless communication, as shown in FIG. 1. Clinician programmer 36 and patient programmer 38 may, for example, communicate via wireless communication with neurostimulator 22 using RF telemetry techniques known in the art. Clinician programmer 36 and patient programmer 38 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

In the application of therapy system 20 shown in FIG. 1, implantation of lead 24 may involve the subcutaneous placement of lead 24 transversely across one or more occipital nerves 12, 14, and/or 16, or a branch of the same, that are causing patient 10 to experience pain.

Figure 2:
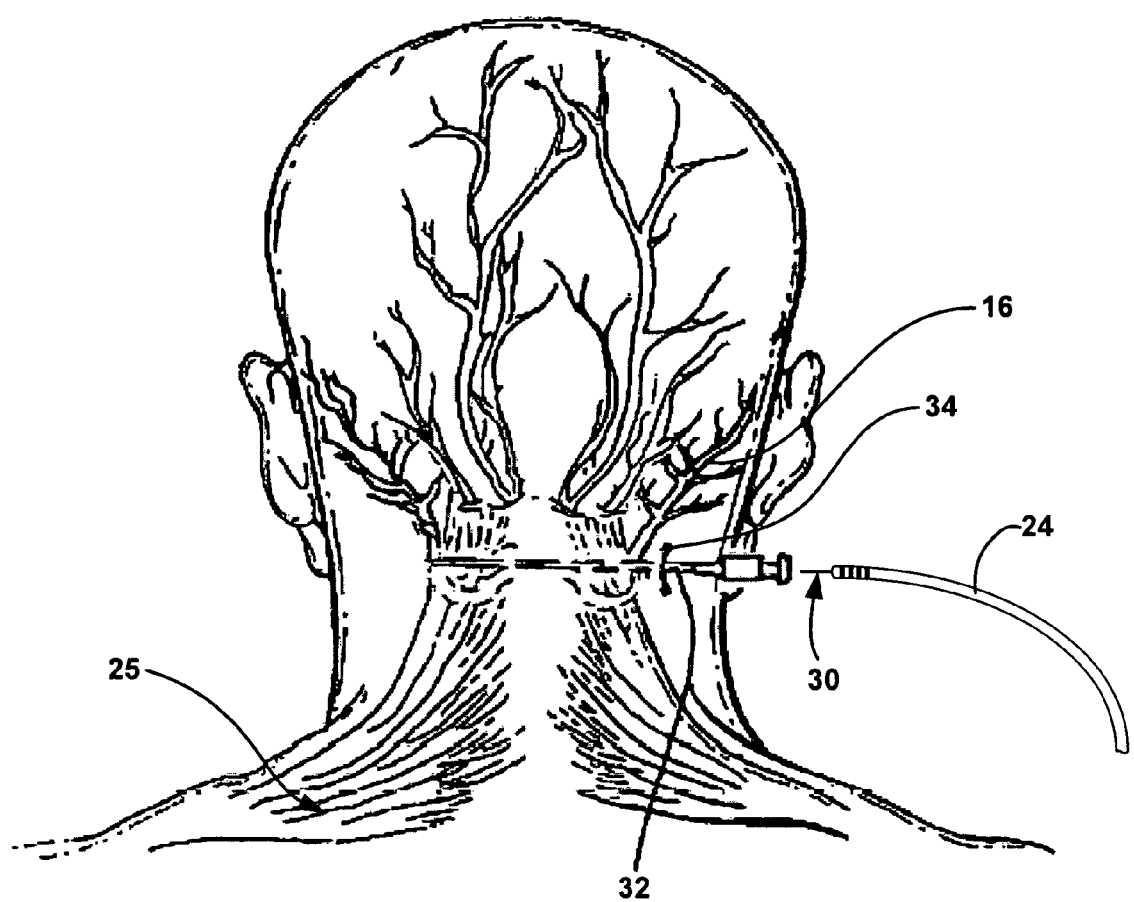
FIG. 2 illustrates the lead of FIG. 1, which is aligned to be introduced into an introducer needle that is positioned proximate to an occipital nerve of the patient.

FIG. 2 illustrates lead 24 and introducer needle 32, which is positioned proximate to target stimulation site 28 of patient 10. Lead 24 is aligned to be introduced into introducer needle 32. In particular, lead 24 is aligned to be implanted and anchored or fixated with actively deployable clip 30 proximate to target stimulation site 28 within patient 10 for stimulation of one or more occipital nerve 12, 14 or 16. In FIG. 2, clip 30 is in an undeployed state and has a substantially straight shape. In order to locate the specific nerve causing pain, a clinician may palpate the area of pain. In addition, some embodiments, a screening lead may be used prior to implanting lead 24 to develop optimal stimulation parameters (e.g., various electrode combinations, amplitude, pulse width or rate).

In one example method of implanting lead 24 proximate to one or more occipital nerves 12, 14, 16, a vertical skin incision 34 approximately two centimeters in length is made in the neck of patient 10 lateral to the midline of the spine at the level of the C1 vertebra. Fluoroscopy may be used to identify the location of the C1 vertebra. Typically, local anesthetic is used during the implantation procedure. The length of vertical skin incision 34 may vary depending on the particular patient. At this location, the patient's skin and muscle are separated by a band of connective tissue referred to as fascia. In another technique, an incision is made in trapezius muscle 25 of patient 10.

Introducer needle 32, which may be a Tuohy needle, is introduced through incision 34 into the subcutaneous tissue, superficial to the fascia and muscle layer but below the skin. In some embodiments, introducer needle 32 may be manually curved by the clinician to conform to the contour of the body of patient 10 proximate to target stimulation site 28, and in the embodiment shown in FIG. 2, the clinician may conform introducer needle 32 to the contour of the neck of patient 10. In other embodiments, introducer needle 32 may have a preformed curve.

Occipital nerves 12, 14, and 16 are located within the cervical musculature and overlying fascia, and as a result, introducer needle 32, and eventually lead 24, are inserted superior to occipital nerves 12, 14, and 16. That is, in one embodiment, introducer needle 32 is introduced into the fascia layer of patient 10 such that introducer needle 32 is between the skin of patient 10 and target stimulation site 28.

Introducer needle 32 may be guided transversely from incision 34 across the midline of the spine of patient 10 to target stimulation site 28. A stylet may be disposed within introducer needle 32 to provide a clinician with a device to manipulate introducer needle 32 with control. Fluoroscopic observation may aid the clinician in identifying the trunk of the occipital nerve. Once introducer needle 32 is fully inserted, a needle stylet may be removed from the introducer needle, if introducer needle 32 includes a stylet. Lead 24 may then be advanced through introducer needle 32 and positioned to allow stimulation of target stimulation site 28. A stylet may also be disposed within lead 24 to help guide lead 24 to target stimulation site 28. The position of lead 28 may be verified via fluoroscopy or another suitable technique. In addition, the clinician may confirm that electrodes 26 proximate to distal end 24B of lead 24 are properly placed with respect to target stimulation site 28. For example, the clinician may provide electrical signals to electrodes 26 and patient 10 may provide feedback relating to the paresthesia coverage.

Upon placement of lead 24, introducer needle 32 may be removed (either before or after confirming the placement of the electrodes 26). Clip 30 may be deployed either before or after withdrawing introducer needle 32 from patient 10. Upon deployment, clip 30 changes shape and engages with surrounding tissue to substantially fix a position of lead 24 proximate to target stimulation site 28. For example, clip 30 of lead 24 may be deployed into tissue adjacent to an occipital nerve 12, 14 or 16). Alternatively, clip 30 of lead 24 may extend around the outer perimeter of an occipital nerve 12, 14 or 16.

Accurate lead placement may affect the success of occipital nerve stimulation, as well as any other tissue stimulation application of therapy system 20. If lead 24 is located too deep, i.e. anterior, in the subcutaneous tissue, patient 10 may experience muscle contractions, grabbing sensations, or burning. Such problems may additionally occur if lead 24 migrates after implantation. Furthermore, due to the location of implanted lead 24 on the back of the neck of patient 10, lead 24 may be subjected to pulling and stretching that may increase the chances of lead migration. For these reasons, fixating lead 24 with clip 30 may be advantageous.

Figure 3:
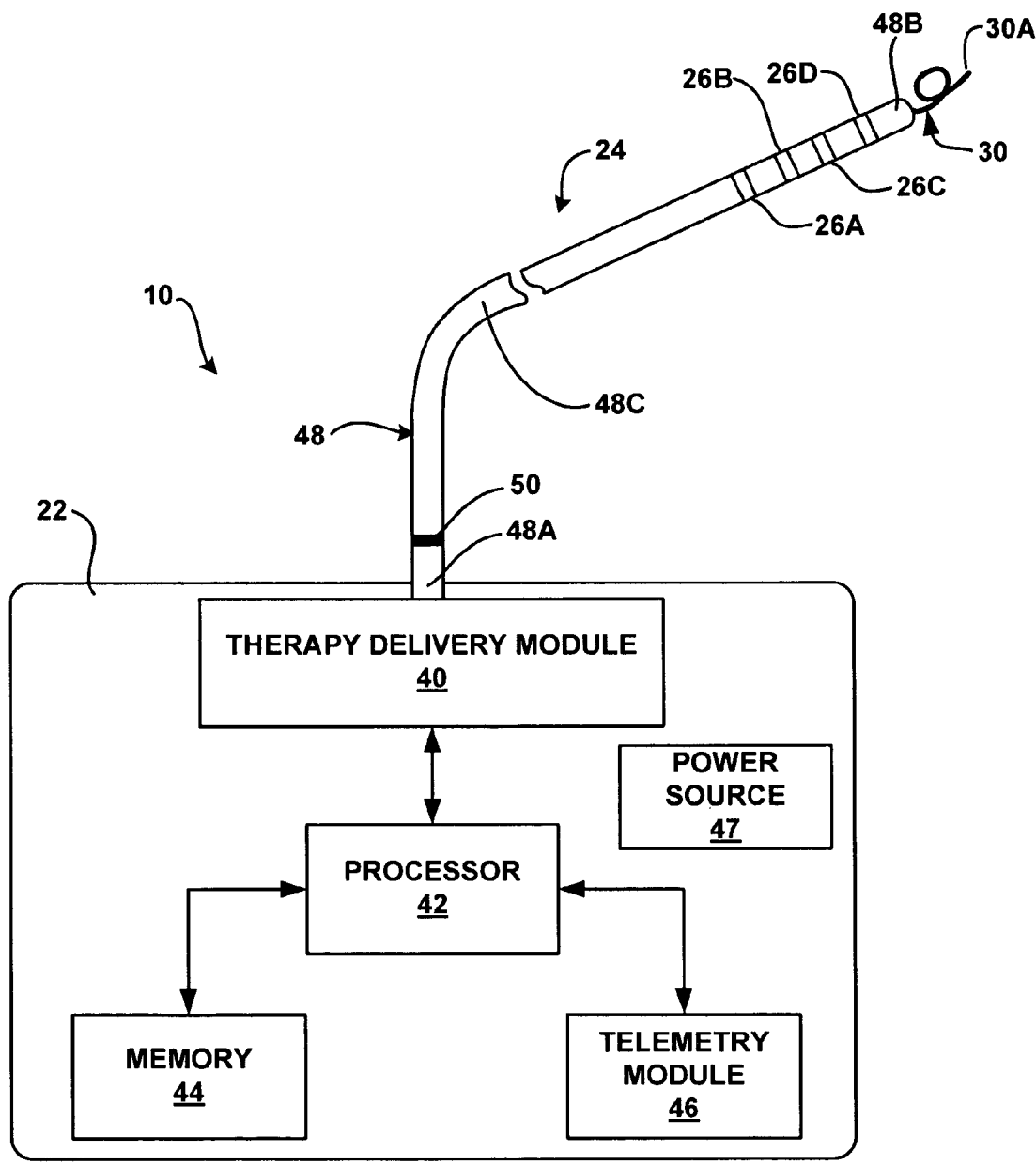
FIG. 3 is a block diagram illustrating various components of an electrical stimulator and the implantable medical lead of FIG. 1.
Figure 11:
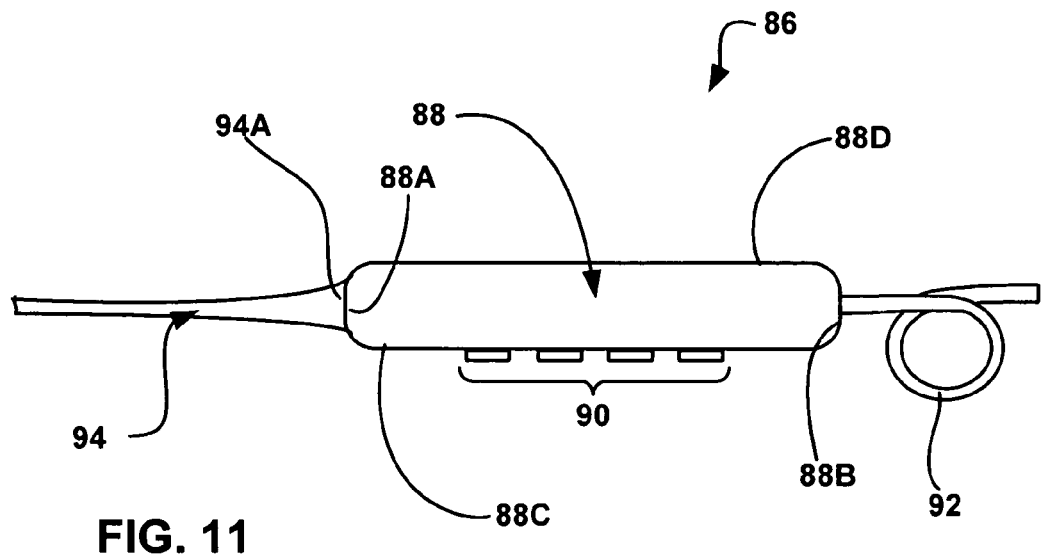
FIGS. 11 and 12 are schematic plan views of paddle leads including actively deployable fixation clips for fixing a position of the paddle lead proximate to a target tissue site in a patient.
Figure 12:
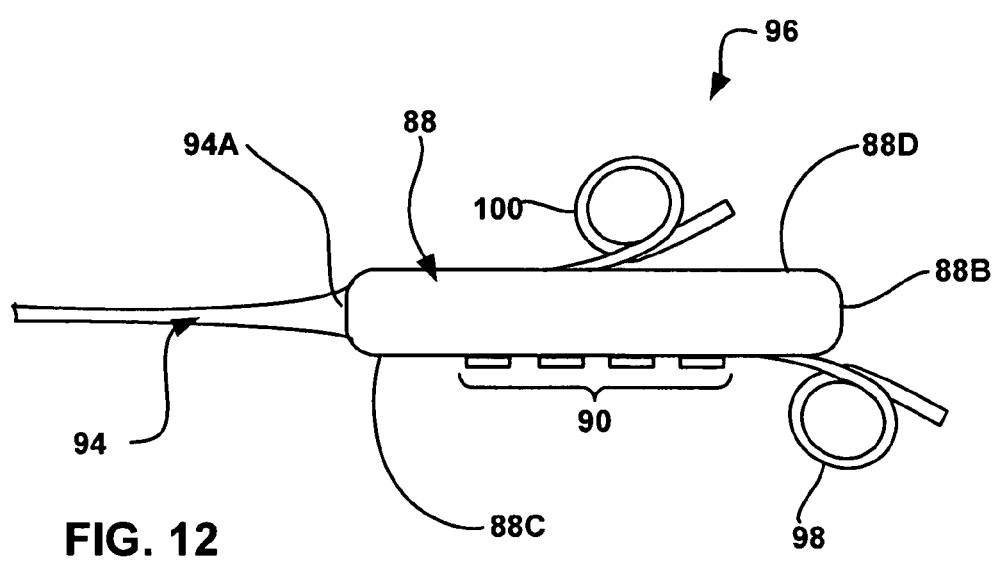

FIG. 3 is a block diagram illustrating various components of neurostimulator 22 and an implantable medical lead 24. Neurostimulator 22 includes therapy delivery module 40, processor 42, memory 44, telemetry module 46, and power source 47. In some embodiments, neurostimulator 22 may also include a sensing circuit (not shown in FIG. 3). Implantable medical lead 24 includes lead body 48 extending between proximal end 48A and distal end 48B. Proximal end 48A of lead body 48, includes contacts (not shown in FIG. 3) to electrically couple lead 24 (and in particular, electrodes 26) to a lead extension or neurostimulator 22 (FIG. 1). In the embodiment of FIG. 3 lead body 48 is cylindrical. In other embodiments, lead body 48 may be paddle-shaped (i.e., a "paddle" lead), in which case lead body 48 would define two opposing surfaces, as shown in FIGS. 11 and 12 with respect to leads 86 and 96, respectively.

Electrodes 26A, 26B, 26C, and 26D (collectively "electrodes 26") are disposed on lead body 48 adjacent to distal end 48B of lead body 48. In some embodiments, electrodes 26 may be ring electrodes. In other embodiments, electrodes 26 may be segmented or partial ring electrodes, each of which extends along an arc less than 360 degrees (e.g., 90-120 degrees) around the circumference of lead body 48. The configuration, type, and number of electrodes 26 illustrated in FIG. 3 are merely exemplary.

In embodiments in which lead 24 is a paddle lead, electrodes 26 may extend along one side of lead body 48. Electrodes 26 extending around a portion of the circumference of lead body 48 or along one side of a paddle lead may be useful for providing an electrical stimulation field in a particular direction/targeting a particular therapy delivery site. For example, in the electrical stimulation application shown in FIG. 1, electrodes 26 may be disposed along lead body 48 such that the electrodes face toward target stimulation site 28 or otherwise away from a scalp of patient 10. This may be an efficient use of stimulation because electrical stimulation of the scalp may not provide any or very minimal useful therapy to patient 10. In addition, the use of segmented or partial ring electrodes 26 may also reduce the overall power delivered to electrodes 26 by neurostimulator 22 because of the efficient delivery of stimulation to target stimulation site 28 by eliminating or minimizing the delivery of stimulation to unwanted or unnecessary regions within patient 10.

In embodiments in which electrodes 26 extend around a portion of the circumference of lead body 48 or along one side of a paddle lead, lead body 48 may include one or more orientation markers 50 proximate to proximal end 48A that indicate the relative location of electrodes 26. Orientation marker 50 may be a printed marking on lead body 48, an indentation in lead body 48, a radiographic marker, or another type of marker that is visible or otherwise detectable (e.g., detectable by a radiographic device) by a clinician. Orientation marker 50 may help a clinician properly orient lead 24 such that electrodes 26 face the desired direction (e.g., toward target stimulation 28) within patient 10. For example, orientation marker 50 may also extend around the same portion of the circumference of lead body 48 or along the side of the paddle lead as electrodes 26. In this way, orientation marker 50 faces the same direction as electrodes 26, thus indicating the orientation of electrodes 26 to the clinician. In one embodiment, when the clinician implants lead 24 in patient 10, orientation marker 50 may remain visible to the clinician.

Neurostimulator 22 delivers stimulation therapy via electrodes 26 of lead 24. In particular, electrodes 26 are electrically coupled to a therapy delivery module 40 of neurostimulator 22 via conductors within lead body 48. In one embodiment, an implantable signal generator or other stimulation circuitry within therapy delivery module 40 delivers electrical signals (e.g., pulses or substantially continuous-time signals, such as sinusoidal signals) to targets stimulation site 28 (FIG. 1) via at least some of electrodes 26 under the control of a processor 42. The implantable signal generator may be coupled to power source 47. Power source 47 may take the form of a small, rechargeable or non-rechargeable battery, or an inductive power interface that transcutaneously receives inductively coupled energy. In the case of a rechargeable battery, power source 47 similarly may include an inductive power interface for transcutaneous transfer of recharge power.

The stimulation energy generated by therapy delivery module 40 may be formulated as neurostimulation energy, e.g., for treatment of any of a variety of neurological disorders, or disorders influenced by patient neurological response. The signals may be delivered from therapy delivery module 40 to electrodes 26 via a switch matrix and conductors carried by lead 24 and electrically coupled to respective electrodes 26.

Processor 42 may include a microprocessor, a controller, a DSP, an ASIC, an FPGA, discrete logic circuitry, or the like. Processor 42 controls the implantable signal generator within therapy delivery module 40 to deliver neurostimulation therapy according to selected stimulation parameters. Specifically, processor 42 controls therapy delivery module 40 to deliver electrical signal s with selected amplitudes, pulse widths (if applicable), and rates specified by the programs. In addition, processor 42 may also control therapy delivery module 40 to deliver the neurostimulation signals via selected subsets of electrodes 26 with selected polarities. For example, electrodes 26 may be combined in various bipolar or multipolar combinations to deliver stimulation energy to selected sites.

Processor 42 may also control therapy delivery module 40 to deliver each stimulation signal according to a different program, thereby interleaving programs to simultaneously treat different symptoms or provide a combined therapeutic effect. For example, in addition to treatment of one symptom such as a migraine headache, neurostimulator 22 may be configured to deliver neurostimulation therapy to treat other symptoms such as back pain.

Memory 44 of neurostimulator 22 may include any volatile or non-volatile media, such as a RAM, ROM, NVRAM, EEPROM, flash memory, and the like. In some embodiments, memory 44 of neurostimulator 22 may store multiple sets of stimulation parameters that are available to be selected by patient 10 via patient programmer 38 (FIG. 1) or a clinician via clinician programmer 36 (FIG. 1) for delivery of neurostimulation therapy. For example, memory 44 may store stimulation parameters transmitted by clinician programmer 36 (FIG. 1). Memory 44 also stores program instructions that, when executed by processor 42, cause neurostimulator 22 to deliver neurostimulation therapy. Accordingly, computer-readable media storing instructions may be provided to cause processor 42 to provide functionality as described herein.

In particular, processor 42 controls telemetry module 46 to exchange information with an external programmer, such as clinician programmer 36 and/or patient programmer 38 (FIG. 1), by wireless telemetry. In addition, in some embodiments, telemetry module 46 supports wireless communication with one or more wireless sensors that sense physiological signals and transmit the signals to neurostimulator 22.

As previously discussed, migration of lead 24 following implantation within patient 10 may be undesirable, and may have detrimental effects on the quality of therapy delivered to patient 10. For example, with respect to the occipital nerve stimulation application shown in FIG. 1, migration of lead 24 may cause displacement of electrodes 26 with respect to target stimulation site 28. In such a situation, electrodes 26 may not be properly positioned to deliver therapy to target stimulation site 28, resulting in reduced electrical coupling, and possibly undermining therapeutic efficacy of the neurostimulation therapy from therapy system 20.

Substantially fixing lead 24 to tissue proximate to target stimulation site 28 near occipital nerves 12, 14, 16 may help prevent lead 24 from migrating from target stimulation site 28 following implantation, which may ultimately help avoid harmful effects that may result from a migrating lead 24. To that end, lead 24 includes actively deployable clip 30.

Actively deployable clip 30 provides a minimally invasive fixation mechanism for substantially fixing lead 24 proximate to target stimulation site 28. As described above with respect to FIG. 2, target stimulation site 28, which may be proximate to occipital nerves 12, 14, 16 or branches thereof, are typically located relatively close to a scalp of patient 10. Accordingly, it may be desirable to provide lead 24 with a fixation element that does not substantially protrude from lead body 48 of lead 24 in order to help minimize interference between the fixation element and the scalp of patient 10. Alternatively, it may be desirable to provide lead 24 with fixation element(s) that extend away from a side of lead body 48 that does not engage with the scalp, epidermis or other integumentary layer of patient 10 when lead 24 is implanted within patient 10. An example of such a fixation element arrangement is described in U.S. patent application Ser. No. 11/591,279 by Martin T. Gerber, entitled, "IMPLANTABLE MEDICAL ELONGATED MEMBER INCLUDING FIXATION ELEMENTS ALONG AN INTERIOR SURFACE," which was filed on Oct. 31, 2006. Minimal interference between clip 30 and the scalp of patient 10 may contribute to the comfort of patient 10 and avoidance of tissue erosion or damage attributable to engagement between clip 30 and the scalp, epidermis or other integumentary layer of patient 10 when lead 24 is implanted in patient 10.

Figure 9:
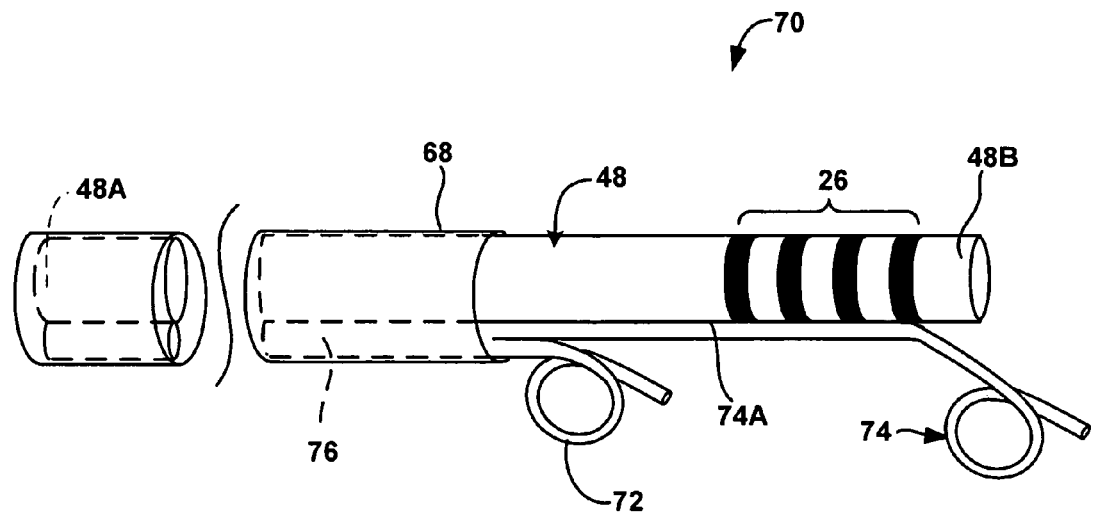
FIG. 9 is a schematic perspective view of another embodiment of a lead, which includes actively deployable clips disposed along the same side of a longitudinal outer surface of a lead body.
Figure 10:
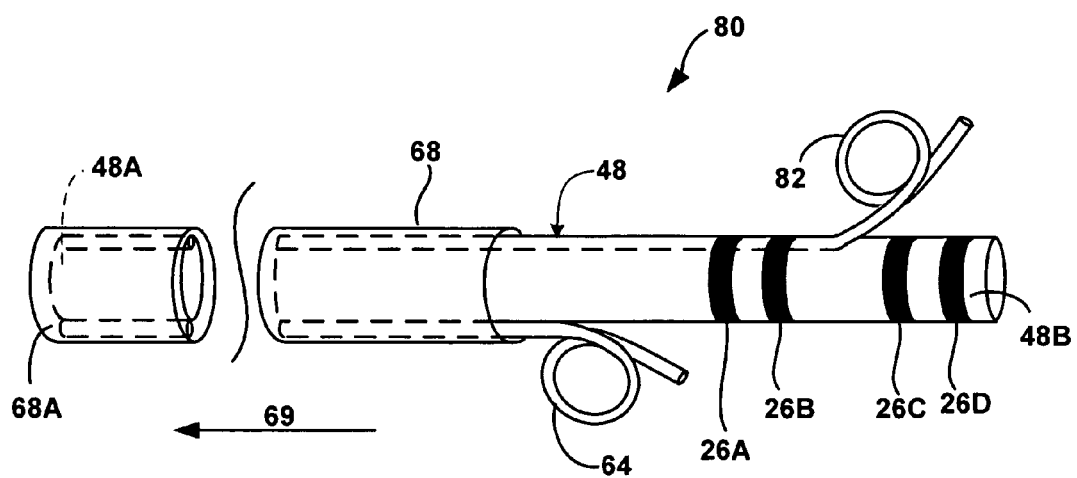
FIG. 10 is a schematic perspective view of another embodiment of a lead, which includes an actively deployable clip extending between electrodes of the lead.

In one embodiment, the deployed clip 30 located at a distal end 48B of lead body 48 is sized such that clip 30 does not protrude past a longitudinal outer surface 48C of lead body 48, which extends between proximal end 48A and distal end 48B, thereby reducing interference between clip 30 and the scalp of patient 10. Even in embodiments in which an actively deployable clip 30 extends from longitudinal outer surface 48C (e.g., as shown in FIGS. 9 and 10), clip 30 may be shaped and sized to minimize interference with the scalp of patient 10. For example, clip 30 may be shaped to have a relatively blunt surface that interacts with the scalp, or clip 30 may be sized such that clip 30 does not engage with the scalp.

In some embodiments, clip 30 may also have a sharp tip 30A that is configured to penetrate into tissue near the target tissue site 28. For example, in embodiments in which lead 24 and clip 30 are implanted proximate to an occipital or trigeminal nerve, tip 30A of clip 30 may be shaped to penetrate through fascia. In embodiments in which tissue ingrowth around clip 30 is desirable, such as when lead 24 is implanted in a region that undergoes a relatively large range of motion or frequent motion, clip 30 may also have a rough outer surface to promote tissue ingrowth. Tissue ingrowth may help further stabilize lead 24. However, in some embodiments, such as when removability of lead 24 is highly desired, tissue ingrowth may be undesirable, in which case clip 30 may be formed to have a relatively smooth outer surface to inhibit tissue adherence.

Figure 4A:
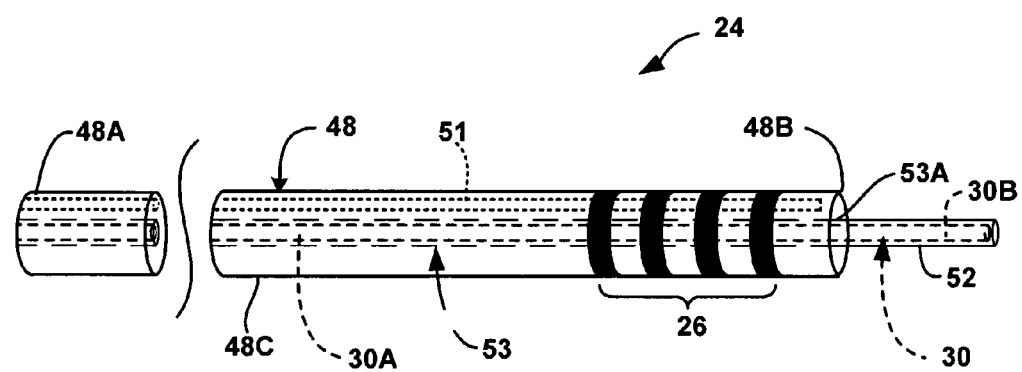
FIG. 4A is a schematic perspective view of the lead of FIG. 1, where a fixation clip of the lead is in an undeployed state.
Figure 4B:
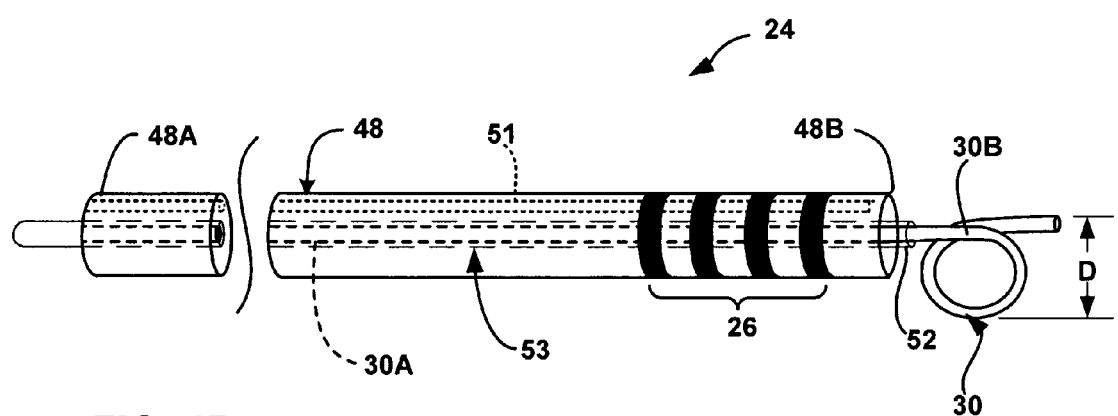
FIG. 4B is a schematic perspective view of the lead of FIG. 1, where the clip is in a deployed state.

FIG. 4A is a schematic perspective view of lead 24, where clip 30 (shown in phantom lines) is in an undeployed state (i.e., a first state), and FIG. 4B is a schematic perspective view of lead 24 with clip 30 in a deployed state (i.e., a second state). Clip 30 includes a first body portion 30A (shown in phantom lines) that extends along the length of lead body 48 and a second portion 30B. First and second body portions 30A and 30B are substantially cylindrical. However, in other embodiments, first body portion 30A and/or second body portion 30B may have any suitable shape. For example, first body portion 30A may be a flat ribbon, which may increase a surface for contacting and engaging with surrounding tissue.

Actively deployable clip 30 may be composed at least in part of an elastically deformable material wire that changes shape, e.g., from a substantially straight or slightly curved shape as shown in FIG. 4A to a moderately or highly curved shape as shown in FIG. 4B. In the embodiment shown in FIG. 4B, second portion 30B of clip 30 has a substantially spiral shape in the deployed state.

In FIG. 4A, clip 30 is retained within retainer mechanism 52, which may be any suitable apparatus that is capable of retaining clip 30, and in particular, second portion 30B of clip 30, in an undeployed state. For example, retainer mechanism 52 may be a sheath, a wrap, introducer needle (e.g., a Tuohy needle) or binder disposed around clip 30 and/or longitudinal outer surface 48C of lead body 48.

Retainer mechanism 52 is disposed within a lumen 53 defined by lead body 48 and substantially surrounds body portion 30A of clip 30. Lumen 53 extends through the length of lead body 48 such that distal end 48B of lead body 48 defines an opening 53A. Retainer mechanism 52 may extend through lumen 53 and opening 53A to surround second portion 30B of clip 30 to help maintain second portion 30B in a substantially undeployed state. In this way, retainer mechanism 52 helps prevent premature activation of clip 30 (e.g., prior to lead 24 reaching target stimulation site 28). In some embodiments, retainer mechanism 52 abuts the outer surface of clip 30, while in other embodiments, there is a clearance between retainer mechanism 52 and clip 30 when retainer mechanism 52 is disposed within lumen 53 of lead body 48. Lead body 48 may also include stylet lumen 51 that extends substantially parallel to lumen 53 and is configured to receive a stylet. During implantation of lead 24 within patient 24, a clinician may manipulate a stylet disposed within stylet lumen 51 to manipulate and bend the distal tip 48B of lead body 48 to guide lead 24 through patient 10 and reach target stimulation site tissue 28.

In an alternate embodiment, clip 30 may not include body portion 30A extending through lead body 48. For example, clip 30 may be attached directly or indirectly to distal end 48B of lead body 48, such as with an adhesive, welding (e.g., ultrasonic welding) or clip 30 may be integrally molded with lead body 48. In another embodiment, body portion 30A of clip 30 may extend only part way through the length of lead body 48 (measured between proximal end 48A and distal end 48B).

When a clinician desires to deploy clip 30, the clinician may axially retract retainer mechanism 52 from lead body 48. Once retainer mechanism 52 is withdrawn past opening 53A in lead body 48 and second portion 30B of clip 30 is released from retainer mechanism 52, second portion 30B of clip 30 assumes a spiral shape in the example of FIG. 4B. The spiral shape increases the outermost dimension D (shown in FIG. 4B) of second portion 30B of clip 30 and enables clip 30 to engage with surrounding tissue. Outermost dimension D is not necessarily the diameter of the second, deployed shape of clip 30 because the second shape of clip 30 may not have a circular cross-section, but in some embodiments, outermost dimension D may be the diameter of the second shape of clip 30. The curvilinear shape of second portion 30B of clip 30 also enables lead 24 to resist both movement in both axial and radial directions, and resist pulling forces from both proximal and distal directions. Lead body 48 may be subjected to a pulling force from proximal end 48A because proximal end 48A is fixed to neurostimulator 22 (FIG. 1). Lead body 48 may also be subject to other types of forces because lead 24 may be implanted in a region of patient 10 (e.g., a neck of patient 10) that undergoes a range of motion.

Other types of restraint mechanisms 52 may be used to restrain clip 30. For example, a wrap or binder that extends about clip 30 to hold it in its unexpanded position may be severed, cut, squeezed or crushed using any of a variety of surgical tools to permit the clip 30 to deploy. In addition, clip 30 may be deployed via any suitable technique in addition to releasing clip 30 from restraint mechanism 52. For example, in one embodiment, first body portion 30A of clip 30 may be disposed within lumen 53, and first body portion 30A may be deployed therefrom by pushing first body portion 30A out of lumen 53 with a stylet disposed within lumen 53.

In some embodiments, the elastically deformable material wire used to form deployable clip 30 may be a shape memory polymer or metal, such as Nitinol (a nickel titanium based alloy). A shape memory polymer or metal may have superelastic and memory properties. The elastically deformable material may include additional elements in addition to Nitinol which affect the yield strength of the material or the temperature at which particular pseudoelastic or shape transformation characteristics occur. The transformation temperature may be defined as the temperature at which a shape memory material finishes transforming from martensite to austenite. Upon heating the elastically deformable material may exhibit pseudoelastic (superelastic) behavior when deformed at a temperature slightly above its transformation temperature. For example, if the elastically deformable material forming clip 30 is a shape memory alloy, a portion of the shape memory alloy may be converted from its austenitic phase to its martensitic phase when clip 30 is in its deployed configuration. As the stress is removed, the elastically deformable material may undergo a martensitic to austenitic conversion and spring back to its original undeformed configuration (i.e., the deployed state of clip 30). For example, a shape memory alloy metal may be formed into an elastically deformable material by first wrapping a wire onto a mandrel and heat treating the wire at approximately 400-500 degrees Celsius for approximately five to thirty minutes. The wire may be then air quenched at room temperature. The mandrel may have a constant diameter or may be conical in shape.

Other biocompatible materials such as stainless steel, titanium or biocompatible polymeric materials may be used to form clip 30. In some embodiments, clip 30 may be formed at least in part of an electrically conductive material, such as an electrically conductive shape memory metal alloy. For example, at least a part of second portion 30B of clip 30 may be electrically conductive. Lead 24 may include an electrical conductor that is configured to electrically connect clip 30 to neurostimulator 22 (or another medical device). Alternatively, body portion 30A of clip 30 may include an electrically conductive material to enable body portion 30A to function as an electrical conductor to electrically connect clip 30 to neurostimulator 22. In either case, proximal end 24A of lead 24 may include an electrical contact that is electrically connected to the electrical conductor (whether it is a separate electrical conductor or body portion 30A of clip 30) to electrically couple electrically conductive clip 30 to neurostimulator 22 or another medical device, such as a sensor.

In this way, actively deployable fixation clip 30 may serve dual functions. First, clip 30 may engage with surrounding tissue to substantially fix a position of lead 24. Second, clip 30 may act as an electrode of lead 24 in addition to or instead of electrodes 26 to deliver stimulation therapy from neurostimulator 22 to target stimulation site 28. As described below in reference to FIG. 5B, given the ability of clip 30 to retain a curvilinear shape in the deployed state, clip 30 may be used as a cuff electrode in embodiments in which clip 30 is at least partially electrically conductive. In some embodiments, clip 30 may be electrically coupled to at least one other electrode 26, and the electrically connected clip and electrode 26 may act as a single electrode. In other embodiments, clip 30 may be independent of electrodes 26 and may be a delivery electrode (i.e., used to deliver stimulation to target tissue site 28). In yet other embodiments, clip 30 may be independent of electrodes 26 and may, for example, act as a return electrode for at least one of electrodes 26 or a sensing electrode that monitors a physiological parameter of the patient.

Figure 5A:
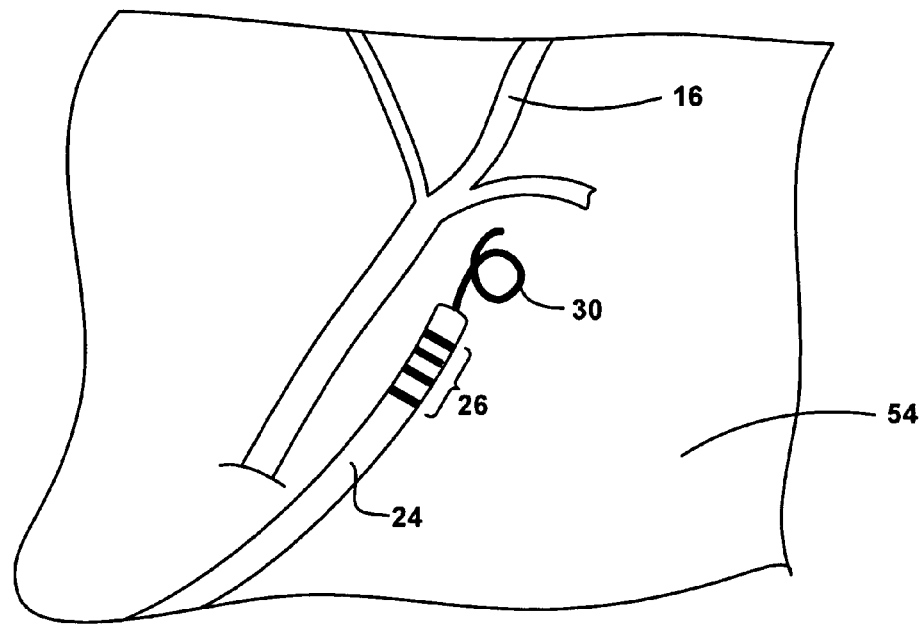
FIG. 5A is a schematic diagram illustrating the lead of FIG. 1 implanted within a patient proximate to an occipital nerve, where the clip has been deployed into tissue adjacent to the occipital nerve.
Figure 5B:
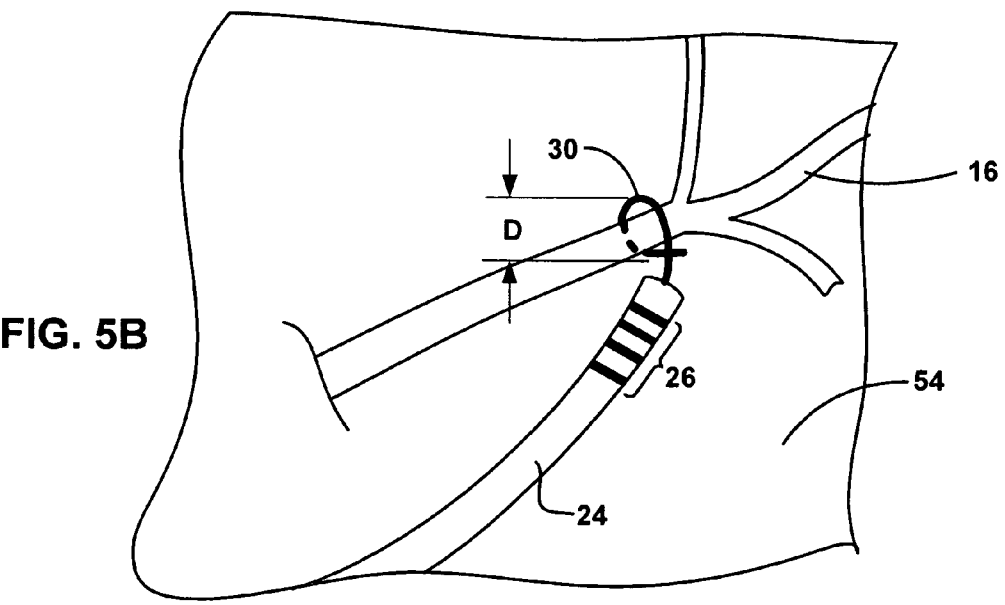
FIG. 5B is a schematic diagram illustrating the lead of FIG. 1 implanted within a patient proximate to an occipital nerve, where the clip has been deployed such that the clip wraps around the occipital nerve.

FIG. 5A is a schematic diagram illustrating lead 24 implanted within patient 10 proximate to third occipital nerve 16. Clip 30 has been deployed into tissue 54 adjacent to third occipital nerve 16 and engages with surrounding tissue 54 to substantially fix electrodes 26 proximate to third occipital nerve 16 to provide electrical stimulation therapy to third occipital nerve 16. Tissue ingrowth may be desirable in such an arrangement between clip 30 and nerve 16. In FIG. 5A (as well as the other figures), the relative positions and sizes of lead 24, electrodes 26, clip 30, and third occipital nerve 16 are merely shown for purposes of illustration and are not intended to be drawn to scale. In general, a certain minimum distance between clip 30 and third occipital nerve 16 is desired in order to help prevent inflammation to third occipital nerve 16, and in some cases, unintended nerve damage. Clip 30 helps maintain the minimum distance between electrodes 26 and third occipital nerve 16. In embodiments in which clip 30 is an electrode of lead 24, clip 30 may also be positioned the minimum distance from third occipital nerve 16.

In FIGS. 5A and 5B, third occipital nerve 16 is shown merely to aid in the description of clip 30, and in other embodiments, lead 24 and clip 30 may be implanted proximate to one or more of the other occipital nerve 12, 14, a branch nerve of occipital nerves 12, 14, 16 or any other nerve, organ, muscle, muscle group or tissue site within patient 10.

FIG. 5B is a schematic diagram illustrating lead and clip 30, which has been deployed around third occipital nerve 16. During implantation, clip 30 may be guided and positioned such that when clip 30 is deployed, clip 30 wraps at least partially around third occipital nerve 16. Contact between clip 30 and third occipital nerve 16 is generally undesirable. Thus, in an embodiment in which clip 30 is deployed around third occipital nerve 16 (or another nerve), the second, deployed state of clip 30 is sized and shaped to wrap around nerve 16 without engaging with third occipital nerve 16. Tissue ingrowth around clip 30 may be undesirable in some embodiments in which clip 30 is deployed around a nerve. In some patients, occipital nerves 12, 14, 16 may each have a diameter of about 1 millimeters (mm) to about 3 mm. Thus, at least with respect to those patients, clip 30 may be sized and shaped such that in a deployed state (FIG. 4B), outermost dimension D of clip 30 is about 4 mm to about 6 mm. However, outermost dimension D of clip 30 in a deployed state may differ depending upon the particular anatomy of patient 10 and the particular size of the nerve to be stimulated.

Deploying clip 30 around third occipital nerve 16 may be useful in embodiments in which clip 30 acts as an electrode for lead 24. By wrapping around at least a part of the outer surface of third occipital nerve 16, clip 30 may be a cuff electrode that provides electrical stimulation therapy to a relatively large surface area of third occipital nerve 16. In addition, the close proximity of an electrically conductive clip 30 to third occipital nerve 16 may also help reduce the power required to deliver the stimulation therapy to third occipital nerve 16. Actively deployable clip 30 provides a clinician with a minimally invasive technique for implanting a cuff electrode around a nerve, such as occipital nerve 12, 14 or 16.

Figure 6A:
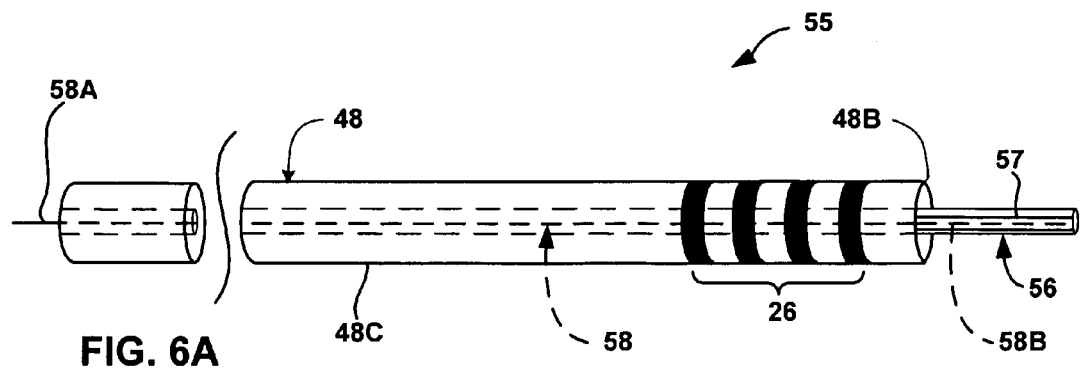
FIGS. 6A-6C are schematic perspective views of a lead including another embodiment of a clip retainer mechanism.
Figure 6B:
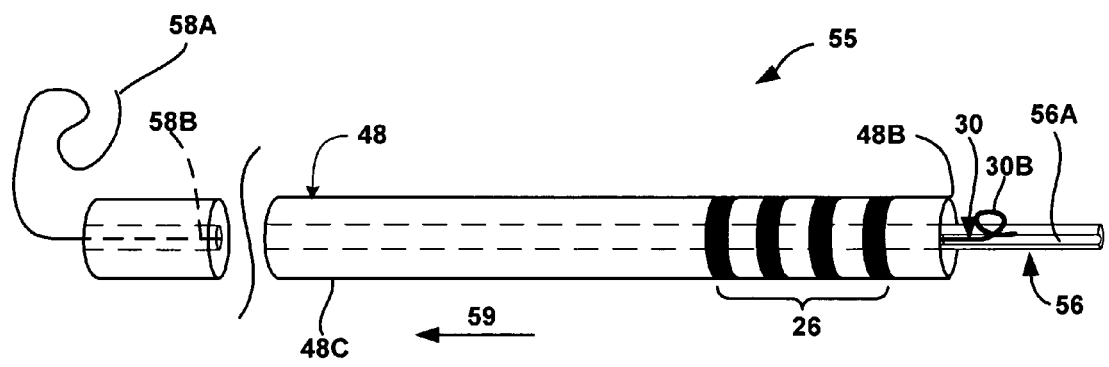
Figure 6C:
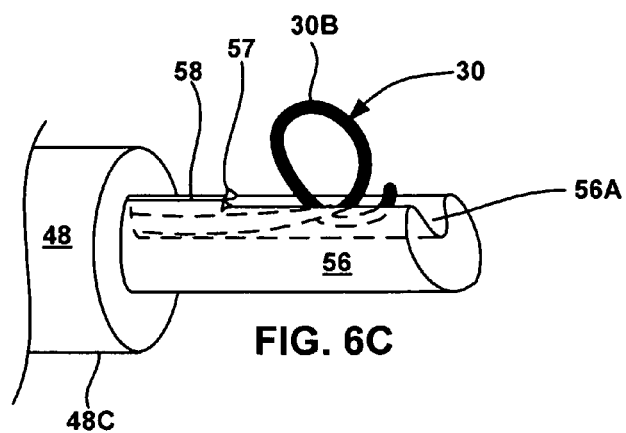

Although a sheath is shown as a retainer mechanism in FIGS. 4A-4B, any suitable retainer mechanism may be used to restrain an actively deployable clip in an undeployed state. FIGS. 6A-C illustrate schematic perspective views of lead 55, which includes another embodiment of a retainer mechanism, and in particular, clip retainer 56. Clip retainer 56 includes a frangible seam 57 and seam breaker 58 that is at least partially embedded within frangible seam 57. Second portion 30B of clip 30 (shown in FIGS. 5B and 5C) is disposed within a cavity 56A (shown in FIGS. 5B and 5C) defined by clip retainer 56. As previously discussed, in some embodiments, clip 30 may be attached to distal end 48B of lead body 48, in which case clip 30 may not include body portion 30A (shown in FIG. 4A), and may only include second portion 30B. Alternatively, clip 30 may be attached to clip retainer 56, which, in the embodiment shown in FIGS. 6A-c, is attached to distal end 48B of lead body 48. In other embodiments, clip retainer 56 may be attached to other portions of lead body 48, such as longitudinal outer surface 48C.

Frangible seam 57 covers cavity 56A of clip retainer 56 in order to help contain second portion 30B of clip 30 within cavity 56A. Frangible seam 57 may be formed of a material that is capable of retaining clip 30 in an undeployed state, but also capable of break upon the application of a force applied by seam breaker 58. For example, frangible seam 57 may be formed of a relatively thin wall polymer, paper, plastic, thin metal, biosorbable materials, or combinations thereof. Similarly, seam breaker 58 is formed of a flexible material that has sufficient strength to break through frangible seam 57. For example, seam breaker 58 may be formed of a polymer, a metal or combinations thereof.

Once lead 55 is positioned proximate to target stimulation site 28, the clinician may actively deploy clip 30 by pulling on proximal end 58A of seam breaker 58. Seam breaker 58 is embedded within frangible seam 57, and is oriented such that when proximal end 58A of seam breaker 58 is pulled in a proximal direction (indicated by arrow 59), distal portion 58B of seam breaker 58 also moves in a proximal direction. As distal portion 58B of seam breaker 58 moves in a proximal direction, distal portion 58B breaks through frangible seam 57. FIG. 6C illustrates how seam breaker 58 opens frangible seam 57 and exposes cavity 56A of clip retainer 56. As shown in FIGS. 6B and 6C, upon the breaking of frangible seam 57, cavity 56A is exposed and clip 30 is released therefrom, thereby enabling body portion 30B of clip to change shape and achieve a deployed state.

FIGS. 1-6C illustrate lead 24 that includes a single clip 30 including second portion 30B that engages with tissue, where the second portion 30B is disposed near distal end 48B of lead body 48 of lead 24. In other embodiments, a lead may include any suitable number of actively deployable clips disposed in any suitable arrangement with respect to a lead body 48 of the lead. Examples of these other arrangements are shown in FIGS. 7-10.

Figure 7:
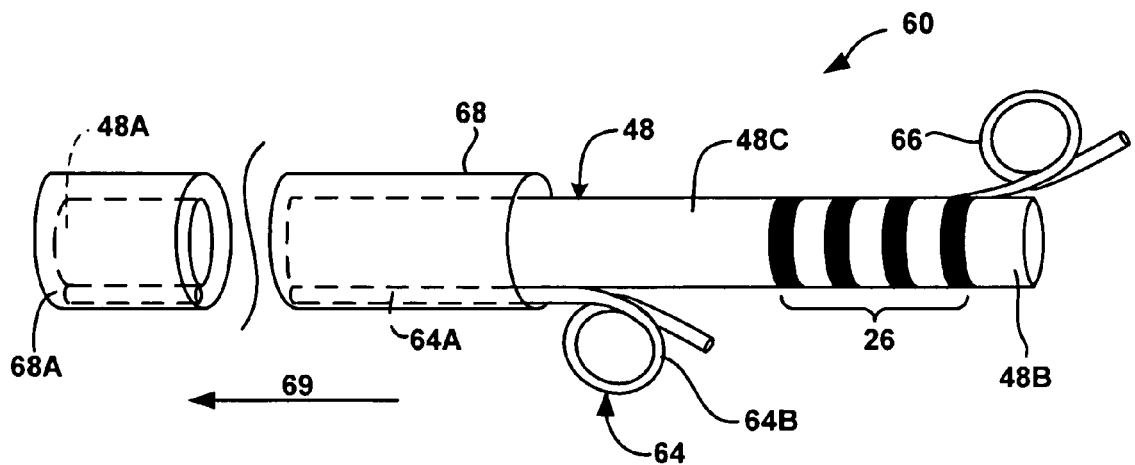
FIG. 7 illustrates a schematic perspective view of another embodiment of a lead, which includes actively deployable clips disposed along a longitudinal outer surface of a lead body.

FIG. 7 illustrates a schematic perspective view of lead 60, which includes actively deployable clips 64 and 66 disposed along longitudinal outer surface 48C of lead body 48. Clips 64 and 66 are shown in their respective deployed states in FIG. 7. Clips 64 and 66 may be used in addition to or instead of clip 30 (shown in FIGS. 4A-6C) on a distal end 48B of lead body 48. Clip 64 is located between electrodes 26 and proximal end 48A of lead body 48, and includes first body portion 64A and second portion 64B. As shown in FIG. 7, when clip 64 is in a deployed state, second portion 64B of clip 64 has a curvilinear shape. Body portion 64A of clip 64 is attached to outer surface 48C of lead body 48 using any suitable technique, such as by an adhesive, welding or body portion 64A of clip 64 and lead body 48 may be integrally molded. In some embodiments, clip 64 may not include body portion 64A, and second portion 64B may be attached (directly or indirectly) to lead body 48, as shown with respect to clip 66, which does not include a body portion that extends along longitudinal outer surface 48C of lead body 48. Clip 66 is located between electrodes 26 and distal end 48B of lead body 48. When clip 66 is in a deployed state, clip 66 also has a curvilinear shape.

As FIG. 7 illustrates, clips 64 and 66 extend from opposite sides of lead body 48. However, in other embodiments, clips 64 and 66 may extend from the same side of lead body 48 (i.e., share a radial position), or alternatively, clips 64 and 66 may have different radial positions with respect to lead body 48.

Clips 64 and 66 need not have the same curvilinear shape or the same size in the respective deployed states. For example, if lead 60 is implanted proximate to occipital nerve 16 in patient 10 such that clip 64 faces a deep direction (away from the scalp of patient 10) and clip 66 faces a superficial direction (towards the scalp of patient 10), it may be desirable for clip 66 to have a smaller outermost dimension in the second, deployed state in order to minimize interference between clip 66 and the scalp of patient 10. As previously discussed, this may help minimize irritation to patient 10 from clip 66 and may help avoid damage to the scalp of patient from clip 66 extending into and possibly through the scalp.

A single restraint mechanism may be used to retain clips 64 and 66 in an undeployed state. For example, in the embodiment shown in FIG. 7, a single introducer needle or single sheath 68 (shown partially withdrawn with respect to distal end 48B of lead body 48) may be disposed around lead 60 and clips 64 and 66 during implantation of lead 60 in patient 10 in order to restrain clips 64 and 66 in the respective undeployed state and prevent premature engagement of clips 64 and 66 with surrounding tissue. In order to deploy clips 64 and 66 into surrounding tissue in order to substantially fix a position of lead 60 with respect to target stimulation site 28 (FIG. 1), sheath 68 may be withdrawn in a proximal direction (as indicated by arrow 69). Axial retraction of sheath 68 may deploy clips 64 and 66 in succession, one at a time, if clips 64 and 66 are at different axial positions along a length of lead 60. Clip 66 is typically deployed before clip 64 if sheath 68 is withdrawn toward proximal end 48A of lead body 48.

Actively deployable clips 64 and 66 may each be formed of a deformable material. When sheath 68 is disposed around lead 60, actively deployable clips 64 and 66 may be compressed, thus minimizing the overall profile of lead 60. Minimizing the profile of lead 60 may help minimize the invasiveness of an implantation procedure for lead 60 because a smaller diameter lead introducer (e.g., introducer needle 32 shown in FIG. 2) may be used to accommodate the smaller profile lead body 60.

Figure 8:
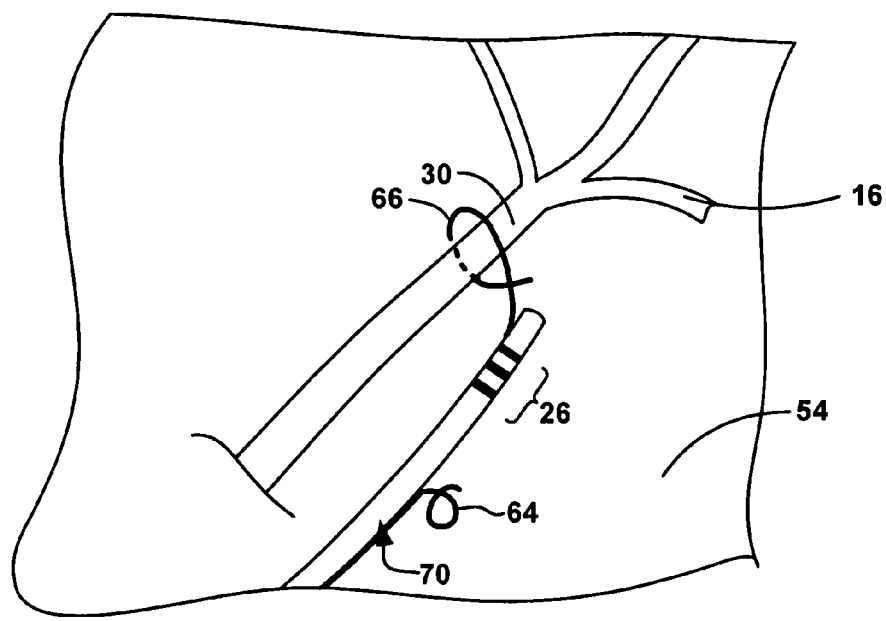
FIG. 8 is a schematic diagram illustrating the lead of FIG. 7 implanted with a patient proximate to an occipital nerve.

FIG. 8 illustrates lead 60 implanted proximate to third occipital nerve 16 of patient 10. When lead 60 includes two or more clips for substantially fixing a position of lead 60 proximate to a target stimulation site, the two or more clips may engage with two different tissue regions, which may provide a more secure fixation of lead 60. For example, in the embodiment shown in FIG. 8, clips 64 and 66 are arranged around lead body 48 such that when deployed, clip 66 may be deployed into tissue adjacent to third occipital nerve 16 and clip 64 may be disposed around third occipital nerve 16. The two fixation points provided by clip 64 and clip 66 proximal to and distal to electrodes 26 may help locally fix electrodes 26 proximate to third occipital nerve 16. In addition, in some embodiments, clip 64 and/or clip 66 may be electrically conductive and may function as electrodes of lead 60.

While lead 60 of FIGS. 7 and 8 includes two actively deployable fixation clips 64 and 66, in other embodiments, a lead may include more than two actively clips. Furthermore, in other embodiments, clips 64 and 66 may not be arranged on opposite sides of lead body 48. For example, FIG. 9 illustrates a schematic perspective view of lead 70, which includes clips 72 and 74 extending from the same side of lead body 48. Clips 72 and 74 share a body portion 76, and clip 74 also includes a body portion 74A that extends from shared body 76. In one technique for forming clips 72 and 74 with a shared body portion 76, a piece of suitable material for forming clips 72 and 74 (e.g., a wire formed from a shape memory material or an elastic material) may be cut to define clips 72 and 74. Body portions 74A and 76 may be coupled to lead body 48 using any suitable means, such as an adhesive, welding or body portions 74A and 76 and lead body 48 may be molded together.

An arrangement including clips 72 and 74 along one side of lead body 48 of lead 70 may be useful when lead 70 is implanted within a subcutaneous region of patient 10 because clips 72 and 74 may be oriented away from the epidermis, scalp or other integumentary layer of patient 10, thereby minimizing interference between clips 72 and 74 and the epidermis, scalp or other integumentary layer. An example of a lead with one or more fixation elements positioned along one side of lead body 48 is described in further detail in U.S. patent application Ser. No. 11/591,279 by Martin T. Gerber, entitled, "IMPLANTABLE MEDICAL ELONGATED MEMBER INCLUDING FIXATION ELEMENTS ALONG AN INTERIOR SURFACE," which was filed on Oct. 31, 2006.

In other embodiments, lead 70 may include clips extending from the same side of lead body 48 that do not share a body portion or that do not have a body portion that extends along the length of lead body 48. For example, clip 72 and/or clip 74 may have a configuration similar to clip 66 of FIG. 7.

A lead may also include actively deployable clips between electrodes 26, as shown in FIG. 10. FIG. 10 illustrates a schematic perspective view of lead 80, which includes actively deployable clip 64 (also shown in FIG. 7) and actively deployable clip 82. Clip 64 is disposed between proximal end 48A of lead body 48 and electrodes 26, while clip 82 is disposed between electrodes 26B and 26C. In another embodiment, lead 80 may also include an actively deployable clips located between distal end 48B of lead body 48 and electrodes 26 or at distal end 48B. Actively deployable clip 82 between electrodes 26B and 26C may help locally fix electrodes 26 proximate to target stimulation site 28. Body portion 82A of actively deployable clip 82 is disposed within lead body 48. In another embodiment, both clips 64 and 82 may be partially disposed within lead body 48.

In each of leads 24, 55, 60, 70, and 80 of FIGS. 4A, 6A, 7, 9, and 10, respectively, lead body 48 is cylindrical. In another embodiment, a lead may include a paddle-like shape portion (i.e. a paddle lead) and may include one or more actively deployable clip fixation elements at a distal end of the paddle-shaped portion and/or along one or more longitudinal surfaces of the paddle-shaped portion.

FIG. 11 is a plan view of paddle lead 86, which includes substantially flat, paddle-like shaped lead body 88 extending between proximal end 88A and distal end 88B and including electrodes 90 and actively deployable fixation clip 92. Proximal end 88A of lead body 88 is coupled to distal end 94A of lead body connector 94. A proximal end (not shown in FIG. 12A) of lead body connector 94 may be direct or indirectly (e.g., via a lead extension) coupled to a neurostimulator (e.g., neurostimulator 22 of FIG. 1) or another medical device. Lead body 88 defines a "paddle" like shape, including first surface 88C and second surface 88D, which is on an opposite side of lead body 88 from first surface 88C.

In the embodiment shown in FIG. 11, electrodes 90 are carried by first surface 88C of lead body 88. In another embodiment, paddle lead 86 may also include electrodes along second surface 88D of lead body 88. Each of the electrodes 90 may be electrically coupled to neurostimulator 22, lead extension or other medical device via electrical conductors disposed within lead body 88 and lead body connector 94. A proximal end (not shown in FIG. 11) of lead body connector 94 may include electrical contacts for electrically connecting the electrical conductors within lead body connector 94 to neurostimulator 22.

Extending from distal end 88B of lead body 88 is actively deployable fixation clip 92, which is shown in its deployed state. Clip 92 may be attached directly or indirectly to distal end 88B of lead body 88, or may have a body portion that extends through lead body 88. When lead 86 is implanted within patient 10, clip 92 may engage with surrounding tissue to substantially fix electrodes 90 proximate to target stimulation site 28. In some embodiments, clip 92 may be at least partially conductive and may be an electrode for lead 86.

FIG. 12 is a plan view of paddle lead 96, which is another embodiment of paddle lead 86 of FIG. 11. Lead 96 includes actively deployable fixation clips 98 and 100 disposed along first and second surfaces 88C and 88D, respectively, of lead body 88. Clips 98 and 100 may be used in addition to or instead of clip 92 on distal end of lead body 88B, as shown in FIG. 11. Furthermore, lead 96 may include only one clip 98 or 100, which may be useful when lead 96 is implanted within a subcutaneous region of patient 10 because fixing lead 96 along one surface 88C or 88D may help minimize interference between clip 98 or 100 and the epidermis, scalp or other integumentary layer of patient 10.

Figure 13:
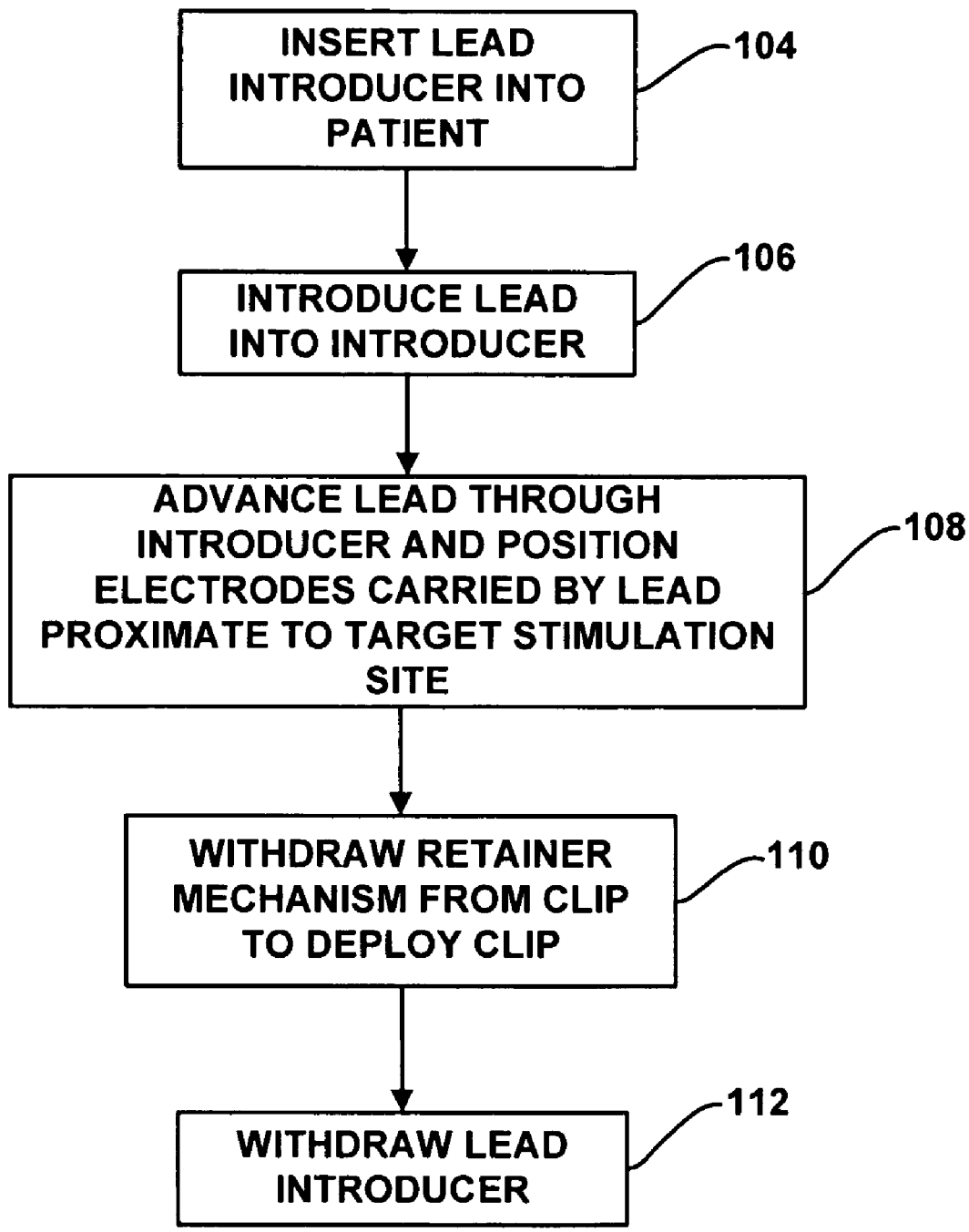
FIG. 13 is a block diagram of a process of implanting a lead including an actively deployable fixation clip within a body of a patient.

FIG. 13 is a flow diagram of a process for implanting a lead 24 (FIGS. 1-5B) including at least one actively deployable fixation clip proximate to one of occipital nerves 12, 14 or 16. While lead 24 is referenced in the description of FIG. 13, it should be understood that the process may also be used to implant any of leads 55, 60, 70, 80, 86 or 96 of FIGS. 6A, 7, 9-12, respectively, or any other lead or implantable medical device including at least one actively deployable fixation clip. Furthermore, in other embodiments, the process illustrated in FIG. 13 may also be used to implant an implantable medical device including a fixation clip proximate to any suitable tissue site within patient 10.

Where treating occipital neuralgia, patient 10 may be placed in a lateral position or in a prone position during implantation of lead 24. Introducer needle 32 (shown in FIG. 2), or another introducer, is introduced into patient 20 (FIG. 1) near target stimulation site 28 (104), and a distal end of introducer needle 32 is guided to target stimulation site 28. Introducer needle 32 may be inserted into patient 10 percutaneously or via an incision (e.g., incision 34 in FIG. 2). As described in reference to FIG. 2, introducer needle 32 may be introduced into subcutaneous tissue, superficial to the fascia and muscle layer of patient 10, but below the skin (or scalp) of patient 10. The clinician may guide introducer needle 32 to a region superior to occipital nerves 12, 14, 16 or another nerve or tissue site to be stimulated. Introducer needle 32 may have a preformed curve to follow the contour of the body of patient 10 at the insertion site, or the clinician may manually curve introducer needle 32.

After introducer needle 32 reaches the desire site within patient (i.e., a location proximate to target stimulation site 28), a stylet may be removed from introducer needle 32 if introducer needle 32 includes a stylet. Lead 24 is then introduced into a lumen of introducer needle 32 (106). In particular, distal end 24B of lead 24 is introduced into the lumen before proximal end 24A. In some embodiments, lead 24 may be preloaded into introducer needle 32, which may eliminate the need to introduce lead 24 into the lumen of introducer needle 32. While clip 30 is in an undeployed state, lead 24 is advanced through the lumen until electrodes 26 adjacent to distal end 48B of lead body 48B of lead 24 are positioned proximate to target stimulation site 28 (108). For example, distal end 24B of lead 24 may be advanced through the lumen of introducer needle 32 until at least distal end 24B protrudes past the lumen and into tissue 54 (FIG. 5A) of patient 10 and undeployed clip 30 protrudes past the distal tip of the introducer. Alternatively, undeployed clip 30 may be introduced into surrounding tissue 54 by at least partially withdrawing introducer needle 32, thereby exposing lead 24. Partially withdrawing introducer needle 32 allows the clinician to reinsert introducer needle 32 if repositioning of lead 24 is desired, while still exposing electrodes 26.

The clinician may confirm that electrodes 26 are operative positioned with respect to target stimulation site 28, such as by providing electrical stimulation to electrodes 26 and receiving feedback from patient 10. Patient 10 may, for example, indicate the level of therapy provided by the electrical stimulation, the area of coverage, and so forth. Alternatively, the clinician may confirm that electrodes 26 are properly positioned with the aid of fluoroscopic imaging.

As discussed above, the clinician may aim to deploy clip 30 around at least a part of an outer perimeter of a target occipital nerve 12, 14, or 16 (or another nerve within patient 10), such as when clip 30 is also an electrically conductive electrode. In such an application of lead 24, the clinician may position clip 30 with respect to the target nerve to achieve such an arrangement of clip 30 (108). Fluoroscopy or another technique may be used to help the clinician precisely and accurately place clip 30 to wrap around at least a part of the nerve.

The clinician may then deploy clip 30 by withdrawing restraint mechanism 52 (FIG. 4A) or otherwise permitting clip 30 to change shape into the deployed state (110). Once deployed, actively deployable clip 30 changes from a substantially straight or slightly curved shape to assume the spiral configuration shown in FIG. 4B. In the deployed shape, clip 30 engages with surrounding tissue to substantially fix a position of lead 24 proximate to target stimulation site 28 and substantially fix electrodes 26 within the tissue to ensure reliable electrical contact with target stimulation site 28. If lead introducer 32 has not been withdrawn from patient 20, the clinician may withdraw the lead introducer 32 after deployment of clip 30 (112).

After securing electrical stimulation lead 24 with actively deployable clip 30, the clinician may connect proximal end 24A of lead 24 to neurostimulator 22. If an implantable neurostimulator 22 is used, the clinician may tunnel proximal end 24A of lead 24 to the implant site for implantable neurostimulator 22. Various modifications to the described techniques of implantation of electrical stimulation lead 24 may be made.

The position, pattern and number of electrodes carried by the various leads described in this disclosure may vary. For example, some leads may carry a single electrode or multiple electrodes. The electrodes may be arranged in a linear array, a two-dimensional array, or a three-dimensional array. The electrodes may take the form of electrode rings, pads, or probes. In addition, the leads may take the form of conventional axial leads with ring electrodes or paddle leads with a two-dimensional array of electrode pads.

Electrodes carried by a given lead may form bipolar or multipolar electrode combinations with electrodes on the same lead or electrodes on a different lead or leads. In addition, such electrodes may form unipolar electrode combinations with one or more electrodes carried by an implantable stimulation generator, e.g., on the housing or "can" in an active can arrangement. In addition, in some embodiments, an electrical stimulation generator may carry integrated electrodes, forming a so-called leadless stimulator or "microstimulator." In each of these cases, a deployable clip as described herein may be utilized to fix a lead, stimulation generator housing, or other implantable medical device relative to a desired target site for delivery of electrical stimulation, drugs or other therapies.

An implantable medical device may include other types of fixation elements in addition to an actively deployable clip. For example, in addition to an actively deployable clip, a lead may also include other actively or passively deployed fixation element that helps prevent migration of the lead when the lead is implanted in patient 10, such as, but not limited to, one or more tines, barbs, hooks, adhesives (e.g., surgical adhesives), balloon-like fixation elements, collapsible or expandable fixation structures, a vacuum-receiving cavity and pinning member, and so forth. The other fixation elements may be composed of any suitable biocompatible material, including, but not limited to, titanium, stainless steel, Nitinol (a nickel titanium based alloy), other shape memory materials, hydrogel or combinations thereof.

A lead including one or more actively deployable fixation clips may be useful for various electrical stimulation systems. For example, the lead may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, muscle stimulation (e.g., functional electrical stimulation (FES) of muscles) or obesity. In addition, an actively deployable clip described herein may also be useful for fixing a catheter, such as a drug deliver catheter, proximate to a target drug delivery site or a microstimulator to a target tissue site within a patient.

Various embodiments of the invention have been described. These and other embodiments are within the scope of the following claims.

The invention claimed is:

1. A system comprising:
   an implantable medical device defining a longitudinal outer surface;
   a stimulation electrode extending at least partially around the longitudinal outer surface of the implantable medical device; and
   a wire fixation element disposed along the longitudinal outer surface of the implantable medical device, wherein only a portion of the fixation element is electrically conductive, the portion being configured to at least one of deliver electrical stimulation to a target tissue site within a patient or sense a physiological parameter from the target tissue site, wherein the fixation element is actively deployable from a first shape to a second shape to resist substantial movement of the implantable medical device from the target tissue site, and wherein the stimulation electrode and the portion of the fixation element are configured to be activated independent of one another.

2. The system of claim 1, wherein the second shape has an outermost dimension of at least about two millimeters.

3. The system of claim 2, wherein the outermost dimension of the second shape is between about two millimeters and about five millimeters.

4. The system of claim 1, further comprising a retainer that retains the fixation element in the first shape, wherein the retainer releases the fixation element for deployment to the second shape in response to manipulation of the retainer.

5. The system of claim 4, wherein the retainer is at least one of a sheath or a device defining a cavity configured to receive the fixation element, the device comprising a frangible seam covering the cavity and a seam breaker member at least partially embedded in the frangible seam.

6. The system of claim 1, wherein the first shape is a substantially straight shape.

7. The system of claim 1, wherein the second shape is a substantially curvilinear shape.

8. The system of claim 7, wherein the second shape is a spiral shape.

9. The system of claim 1, wherein the stimulation electrode comprises a first stimulation electrode and the implantable medical device is a lead comprising at least the first stimulation electrode, and wherein at least a portion of the electrically conductive portion of the fixation element is a second stimulation electrode of the lead.

10. The system of claim 9, wherein the second stimulation electrode is a cuff electrode configured to wrap around at least one of an occipital nerve or a trigeminal nerve of the patient.

11. The system of claim 9, further comprising an electrical stimulation generator coupled to the lead, the fixation element being configured to deliver electrical stimulation from the electrical stimulation generator to the tissue site within the patient.

12. The system of claim 9, wherein the fixation element comprises a first fixation element located between the distal end of the lead and the first stimulation electrode, the system further comprising a second fixation element located between a proximal end of the lead and the first stimulation electrode.

13. The system of claim 9, wherein the lead further comprises a third stimulation electrode adjacent to the first stimulation electrode, the third stimulation electrode extending at least partially around the longitudinal outer surface of the lead body, wherein the fixation element is located between the first and third stimulation electrodes.

14. The system of claim 1, wherein the fixation element is attached to a distal end of the implantable medical device.

15. The system of claim 1, wherein the fixation element comprises one of an elastic material or a shape memory material.

16. The system of claim 1, wherein the implantable medical device comprises an electrical stimulation generator.

17. The system of claim 1, wherein the longitudinal outer surface of the implantable medical device is round and the electrode extends at least partially around a circumference of the longitudinal outer surface.

18. The system of claim 1, wherein the stimulation electrode comprises at least one or a ring electrode, a partial ring electrode or a segmented electrode.

19. The system of claim 1, wherein the implantable medical device comprises a lead body comprising a substantially flat paddle-like shape comprising first and second opposing major surfaces, wherein the stimulation electrode and the wire fixation element are disposed on one of the first or second major surfaces.

20. The system of claim 19, wherein the fixation element comprises a first fixation element disposed along the first major surface of the substantially flat paddle-like lead body between the distal end and the stimulation electrode, the system further comprising a second fixation element disposed along the second major surface of the substantially flat paddle-like lead body.

21. The system of claim 19, wherein the fixation element is attached to a distal end of the substantially flat paddle-like lead body.

22. A medical lead comprising:
a lead body defining a longitudinal outer surface;
an electrical conductor disposed within the lead body;
a stimulation electrode extending at least partially around the longitudinal outer surface of the lead body; and
a wire fixation element, wherein only a portion of the wire fixation element is electrically conductive, the portion being electrically coupled to the electrical conductor and disposed along the longitudinal outer surface of the lead body, wherein the fixation element is actively deployable from a first shape to a second shape to resist substantial movement of the lead body from a target therapy delivery site in a patient, and wherein the stimulation electrode and the portion of the fixation element are configured to be activated independent of one another.

23. The medical lead of claim 22, wherein the fixation element is a first electrode and the stimulation electrode comprises a second electrode carried by the lead body.

24. The medical lead of claim 23, wherein the fixation element comprises a first fixation element located distal to the second electrode and the medical lead further comprises a second fixation element located proximal to the second electrode.

25. The medical lead of claim 23, wherein at least one of the first or second electrodes is a sensing electrode.

26. The medical lead of claim 22, wherein the second shape is a substantially curvilinear shape.

27. The medical lead of claim 22, wherein the portion of the fixation element is a cuff electrode configured to wrap around a peripheral nerve of a patient.

28. The medical lead of claim 27, wherein the peripheral nerve at least one of an occipital nerve or a trigeminal nerve of the patient.

29. A method comprising:
implanting an implantable medical device in a body of a patient, the implantable medical device defining a longitudinal outer surface and comprising a stimulation electrode extending at least partially around the longitudinal outer surface; and
actively deploying a wire fixation element disposed along the longitudinal outer surface of the implantable medical device, wherein only a portion of the fixation element is electrically conductive, the portion being configured to at least one of deliver electrical stimulation to a target tissue site within the body of the patient or sense a physiological parameter from the target tissue site, wherein the fixation element is actively deployable from a first shape to a second shape to resist substantial movement of the implantable medical device from the target tissue site, and wherein the stimulation electrode and the electrically conductive portion or the fixation element are configured to be activated independent of one another.

30. The method of claim 29, further comprising releasing the fixation element from a retainer for deployment to the second shape.

31. The method of claim 30, wherein releasing the fixation element from the retainer comprises withdrawing a sheath from around the fixation element.

32. The method of claim 30, wherein the retainer defines a cavity and the retainer comprises:
a frangible seam covering the cavity; and
a seam breaker member at least partially embedded in the frangible seam, the fixation element being disposed within the cavity,
wherein releasing the fixation element from the retainer comprises pulling the seam breaker member to break the frangible seam.

33. The method of claim 29, wherein the stimulation electrode comprises a first stimulation electrode and the implantable medical device comprises a lead comprising at least the first stimulation electrode, wherein the fixation element is a second stimulation electrode of the lead.

34. The method of claim 29, further comprising positioning the fixation element with respect to a nerve of a patient such that when the fixation element deploys to the second shape, the fixation element wraps around at least a portion of the nerve.

35. A system comprising:
an implantable medical device defining an outer surface;
a stimulation electrode extending at least partially around the outer surface of the implantable medical device; and
a fixation element coupled to the implantable medical device, the fixation element comprising an electrically conductive portion configured to at least one of deliver electrical stimulation to a target tissue site within a patient or sense a physiological parameter from the target tissue site,
wherein the fixation element is actively deployable from a first shape to a second shape to resist substantial movement of the implantable medical device from the target tissue site, and
wherein the first shape is a substantially straight shape and the fixation element does not protrude past the outer surface of the implantable medical device when deployed to the second shape.

* * * * *